US009885075B2

United States Patent
Viovy et al.

(10) Patent No.: US 9,885,075 B2
(45) Date of Patent: Feb. 6, 2018

(54) METHOD AND DEVICES FOR DETECTING MACROIONS IN A LIQUID MEDIUM

(71) Applicants: CENTRE NATIONAL DE LA RECHERCHE SCIENTIFIQUE, Paris (FR); INSTITUT CURIE, Paris (FR); UNIVERSITE PIERRE ET MARIE CURIE, Paris (FR)

(72) Inventors: Jean-Louis Viovy, Paris (FR); François Amblard, Paris (FR); Laurent Malaquin, Linas (FR); Bastien Venzac, Le Mee sur Seine (FR); Mohamed Lemine Diakite, Grenoble (FR); Stephanie Descroix, Paris (FR); Ismaïl Cisse, Aubervillers (FR); Ulrich Bockelmann, Paris (FR)

(73) Assignees: CENTRE NATIONAL DE LA RECHERCHE SCIENTIFIQUE, Paris (FR); INSTITUT CURIE, Paris (FR); UNIVERSITE PIERRE ET MARIE CURIE, Paris (FR)

( * ) Notice: Subject to any disclaimer, the term of this patent is extended or adjusted under 35 U.S.C. 154(b) by 225 days.

(21) Appl. No.: 14/412,520

(22) PCT Filed: Jul. 2, 2013

(86) PCT No.: PCT/IB2013/055409
§ 371 (c)(1),
(2) Date: Jan. 2, 2015

(87) PCT Pub. No.: WO2014/006561
PCT Pub. Date: Jan. 9, 2014

(65) Prior Publication Data
US 2015/0191773 A1 Jul. 9, 2015

(30) Foreign Application Priority Data
Jul. 2, 2012 (EP) .................................. 12305795.2

(51) Int. Cl.
| | |
|---|---|
| C12Q 1/68 | (2006.01) |
| G01N 21/17 | (2006.01) |
| G01N 30/00 | (2006.01) |
| G01N 33/487 | (2006.01) |
| G01N 15/06 | (2006.01) |
| G01N 15/00 | (2006.01) |

(52) U.S. Cl.
CPC .......... *C12Q 1/686* (2013.01); *C12Q 1/6825* (2013.01); *G01N 15/0656* (2013.01); *G01N 21/17* (2013.01); *G01N 30/00* (2013.01); *G01N 33/48721* (2013.01); *G01N 2015/0038* (2013.01)

(58) Field of Classification Search
None
See application file for complete search history.

(56) References Cited

U.S. PATENT DOCUMENTS

| | | | |
|---|---|---|---|
| 2002/0039743 A1 | 4/2002 | Hashimoto et al. | |
| 2002/0070114 A1 | 6/2002 | Miles | |
| 2003/0057094 A1 | 3/2003 | Bryning et al. | |
| 2005/0136466 A1 | 6/2005 | Miles et al. | |
| 2006/0207891 A1* | 9/2006 | Althaus ................ | C12Q 1/6825 205/787 |
| 2010/0203580 A1 | 8/2010 | Bryning et al. | |

FOREIGN PATENT DOCUMENTS

JP    2003-527601 A    9/2003

OTHER PUBLICATIONS

Jan. 13, 2014 International Search Report issued in PCT/IB2013/055409.
Jan. 13, 2014 Written Opinion of the International Searching Authority issued in PCT/IB2013/055409.
Dec. 11, 2012 European Search Report issued in European Patent Application No. 12 30 5795.
Ferguson, Brian S. et al., "Integrated Microfluidic Electrochemical DNA Sensor", vol. 81, No. 15, pp. 6503-6508, Aug. 1, 2009.
Duffy, David C., et al., Rapid Prototyping of Microfluidic Systems in Poly(dimethylsiloxane), vol. 70, pp. 497-4984, No. 23, Dec. 1, 1998, Analytical Chemistry.
Deféver, Thibault., et al. JACS Articles "Real-Time Electrochemical Monitoring of the Polymerase Chain Reaction by Mediated Redox Catalysis" vol. 131, No. 32, pp. 11433-11441, Feb. 22, 2009.
Li, Jingyi, et al. "Pinwheel Assay Via a 'Pipet, Aggregate and Blot' (PAB) Approach on Filter Paper", pp. 1959-1961, Oct. 2-6, 2011.
Hirons, et al., "Toto and Yoyo: New Very Bright Fluorochromes for DNA Content Analyses by Flow Cytometry", Cytometry 15: pp. 129-140, 1994.
Stegger, et al., "Rapid detection, differentiation and typing of methicillin-resistant *Staphylococcus aureus* harbouring either mecA or the new mecA homologue mecALGA251 ", vol. 18, No. 4, pp. 395-400, Nov. 4, Apr. 2012.
Marino, Michael S. et al., "Spectral Measurements of Intercalated PCR-Amplified Short Tandem Repeat Alleles", vol. 70, No. 21, pp. 4514-4519, Nov. 1, 1998.

(Continued)

*Primary Examiner* — David Thomas
(74) *Attorney, Agent, or Firm* — Oliff PLC

(57) ABSTRACT

The present invention concerns a method of detecting macroions in a liquid medium contained in a space, the method including: a) submitting the liquid medium to a stimulating electrical field to induce formation of aggregates of macroions, the formed aggregates of macroions preferably not including any additional labeling agent, and b) measuring, in a detection zone of the space, spatial and/or temporal fluctuations within the liquid medium of at least one variable depending on the concentration of the macroions in the liquid medium, and c) determining, based on these fluctuations, the presence of the macroions, step c) preferably including processing by a time-dependent or space dependent analysis, more preferably by wavelet analysis, or by autocorrelation the fluctuations measured at step b).

36 Claims, 16 Drawing Sheets

(56) References Cited

OTHER PUBLICATIONS

Mo, Jinyuan, et al., "An on-column miniature conductivity cell and a photocouple separator for conductivity detection by capillary electrophoresis", Anal. Communication, pp. 365-367, Sep. 1998.
Asiello, Peter J., et al. "Miniaturized isothermal nucleic acid amplification, a review", Cite this: Lab Chip, 2011, 11, 1420, www.rsc.org/loc, pp. 1420-1430, Feb. 2011 Journal of Royal Society of Chemistry.
Yager, Paul et al., "Microfluidic diagnostic technologies for global public health", Nature vol. 442 No. 27, pp. 412-418, Jul. 2006.
Mohamed Lemine Youba Diakite et al., "A low-cost, label-free Dna detection method in lab-on-chip format based on electrophydrodynamic instabilities, with application to long-range PCR", Lab on a Chip, vol. 12, No. 22, Jan. 1, 2012, pp. 4738-4747 XP055043156.
Guijt Rosanne M., et al., "Conductivity detection for conventional and miniaturised capillary electrophoresis systems", vol. 25 pp. 4032-4057, Electrophoresis 2004.
Harismendy, Olivier et al., "Evaluation of next generation sequencing platforms for population targeted sequencing studies", Genome Biology, vol. 10, Issue 3, Article R32, pp. 1-13, Published: Mar. 27, 2009.
Isambert, H., et al., "Electrohydrodynamic patterns in macroion dispersions under a strong electric field", vol. 56, No. 5, pp. 5688-5704, Nov. 1997 The American Physical Society.
Niemz, Angelika., et al., "Point-of-care nucleic acid testing for infectious diseases", vol. 29, No. 5, pp. 240-250, Trends in Biotechnology, May 2011.
Nilsson, Mats, et al., "Real-time monitoring of rolling-circle amplification using a modified molecular beacon design", vol. 30 No. 14, pp. 1-7, Nucleic Acids Research, 2002.
Magnúsdóttir, Soffia et al., "Electrohydrodynamically Induced Aggregation During Constant and Pulsed Field Capillary Electrophoresis of DNA", Biopolymers, vol. 49, 385-401 (1999).
Prest, Jeff E., "Bidirectional isotachophoresis on a planar chip with integrated conductivity detection", Analyst, 2002, 127, pp. 1413-1419.
Mitnik L., et al., "Segregation in DNA Solutions Induced by Electric Felds", vol. 267, No. 5195, pp. 219-222, Jan. 13, 1995.
Solinova, Veronika et al., "Recent applicatins of conductivity detection in capillary and chip electrophoresis", J. Sep. Sci. 2006, vol. 29, pp. 1743-1762.
Asbury Charles L., et al., "Trapping of DNA by Dielectrophoresis", Electrophoresis, Wiley Interscience, DE, vol. 23, No. 16, Jan. 1, 2002 pp. 2658-2666, XP003009262.
Asbury C., et al., "Trapping of DNA in Nonuniform Oscillating Electric Fields", Biophysical Journal, Biophysical Society, US. vol. 74, No. 2, Feb. 1, 1998, pp. 1024-1030, XP003009260.
Jun. 13, 2017 Office Action issued in Japanese Application No. 2015-519468.

* cited by examiner

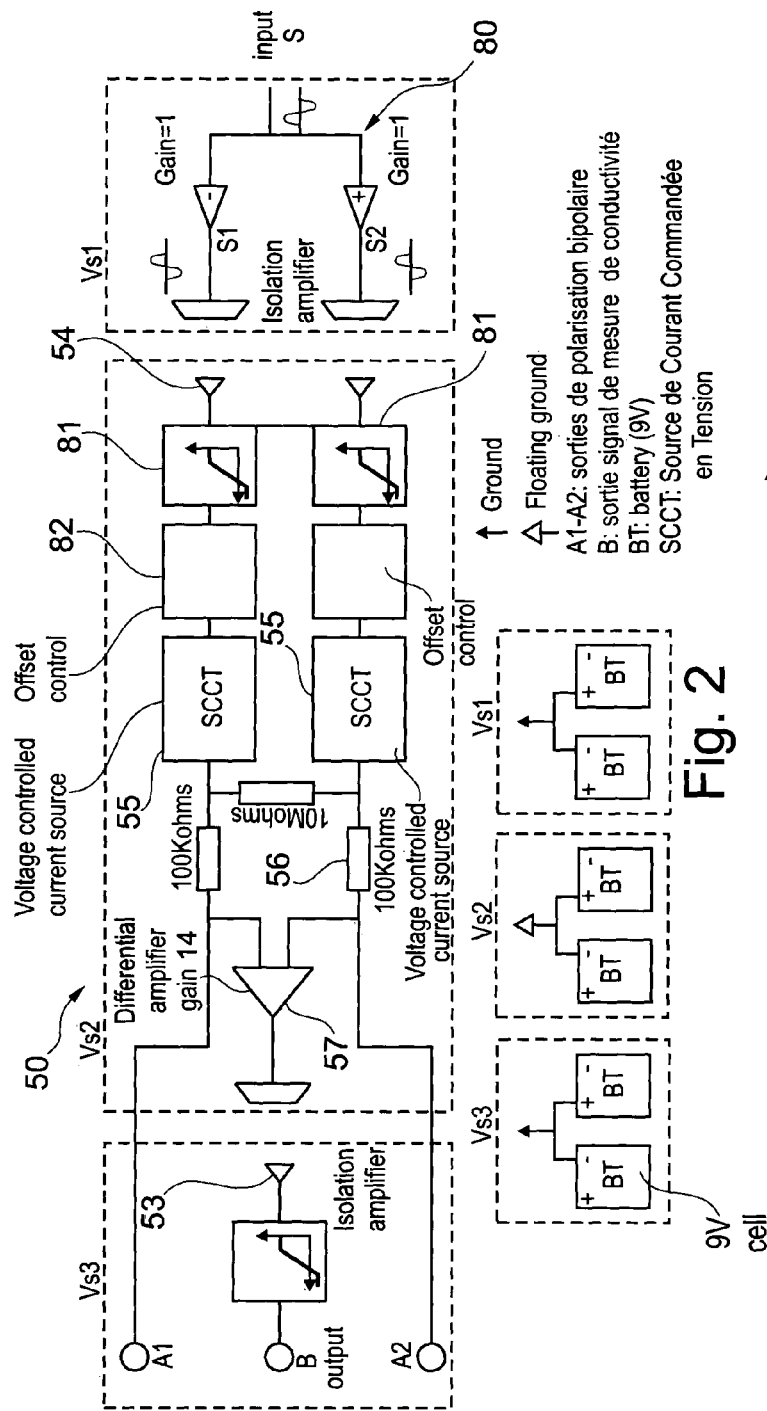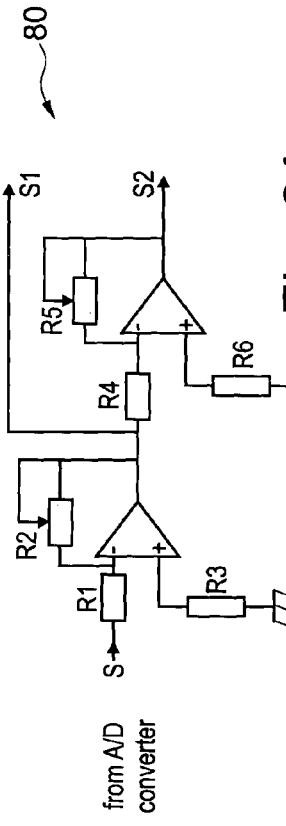

Samples preparation: 1/10 Long range PCR Product (7μl)+SYBRGreen 100x(1μl)+Loading Dye 6x(2μl)
Electrophoretic conditions: 0,7% agarose gel(90min, 100V, 77mA)
☐Densitometric Area (145 square inches)

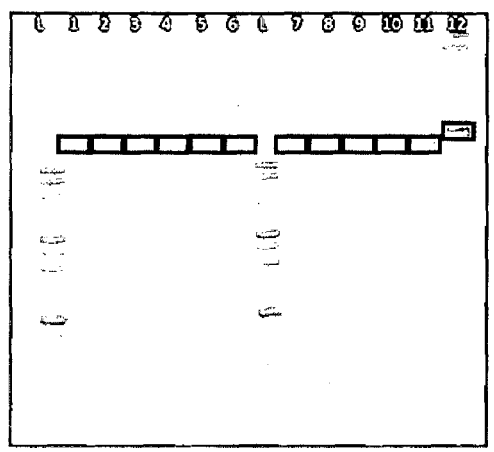

L:1Kb DNA Ladder
1 to 6: 10 cycles of amplification
-x10 (01)-DNAλ:Negative Control
-x10 (02)-DNAλ:10 fg
-x10 (03)-DNAλ:100 fg
-x10 (04)-DNAλ: 1 fg
-x10 (05)-DNAλ: 100 pg
-x10 (06)-DNAλ: 2.5 ng L:1Kb DNA Ladder
7 to 12: 20 cycles of amplification
-x20 (07)-DNAλ:Negative Control
-x20 (08)-DNAλ:10 fg
-x20 (09)-DNAλ:100 fg
-x20 (10)-DNAλ: 1 fg
-x20 (11)-DNAλ: 100 pg
-x20 (12)-DNAλ: 2.5 ng

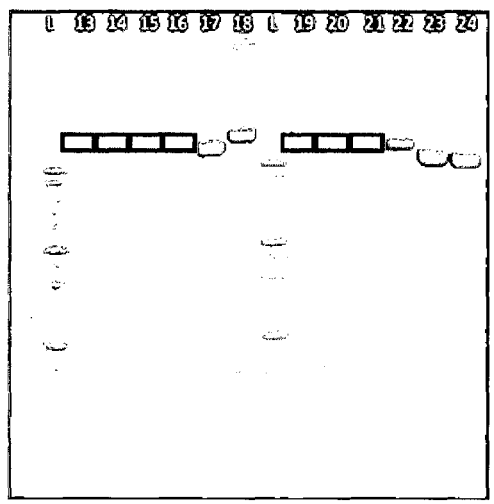

L:1Kb DNA Ladder
13 to 18: 26 cycles of amplification
- (13)-DNAλ:Negative Control
- (14)-DNAλ:10 fg
- (15)-DNAλ:100 fg
- (16)-DNAλ: 1 fg
- (17)-DNAλ: 100 pg
- (18)-DNAλ: 2.5 ng L:1Kb DNA Ladder
19 to 24: 32 cycles of amplification
- (19)-DNAλ:Negative Control
- (20)-DNAλ:10 fg
- (21)-DNAλ:100 fg
- (22)-DNAλ: 1 fg
- (23)-DNAλ: 100 pg
- (24)-DNAλ: 2.5 ng

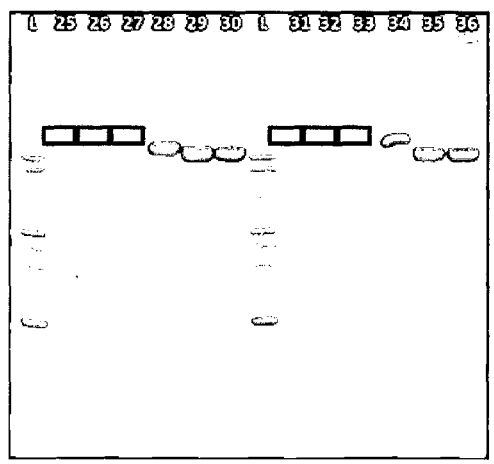

L:1Kb DNA Ladder
25 to 30: 38 cycles of amplification
- (25)-DNAλ:Negative Control
- (26)-DNAλ:10 fg
- (27)-DNAλ:100 fg
- (28)-DNAλ: 1 fg
- (29)-DNAλ: 100 pg
- (30)-DNAλ: 2.5 ng L:1Kb DNA Ladder
31 to 36: 41 cycles of amplification
- (31)-DNAλ:Negative Control
- (32)-DNAλ:10 fg
- (33)-DNAλ:100 fg
- (34)-DNAλ: 1 fg
- (35)-DNAλ: 100 pg
- (36)-DNAλ: 2.5 ng

Fig. 9C

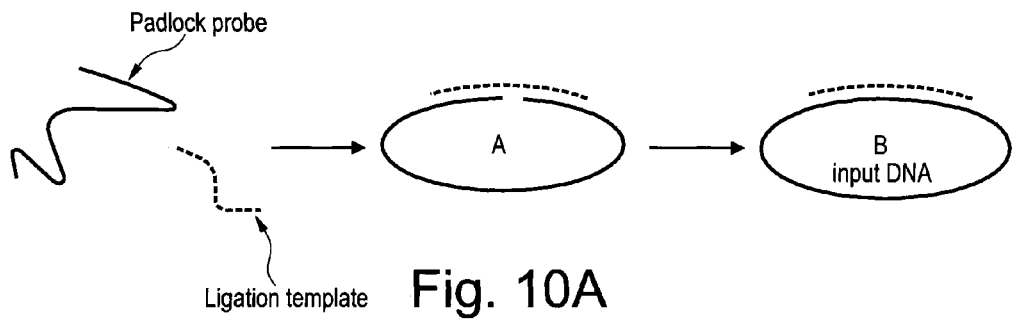

Fig. 10A

```
    nom
ppWT  p-CTGCCATCTTAACAAAC CCTTTCCTCTATGATTACTGACCTACGACCTCAATGCTGCTGCTGT ACTACTCT
 |W|  TCTATG CGATTACCGGGCT
      GTTTGTTAAGATGGCAG AGCCCGGTAATCG
```

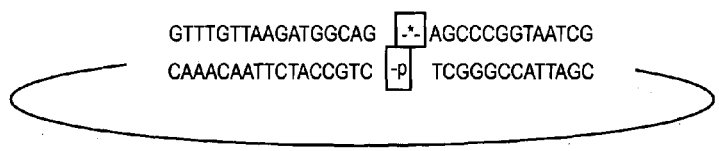

Fig. 10B

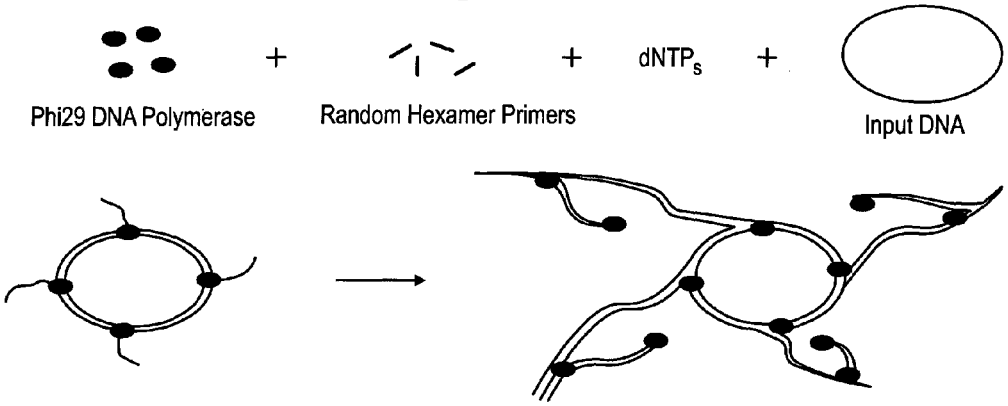

Fig 1.Schematic of the TempliPhi process.Random hexamer primers anneal to the circular template DNA at multiple sites φ29 DNA polymerase extends each of these primers.When the DNA polymerase reaches a downstream extended primer, stand displacement synthnesis occurs.The displaced strand is rendered single-stranded and available to be primed by more hexamer primer.The process continues,resulting in exponential, isothermal amplification.

Fig. 10C

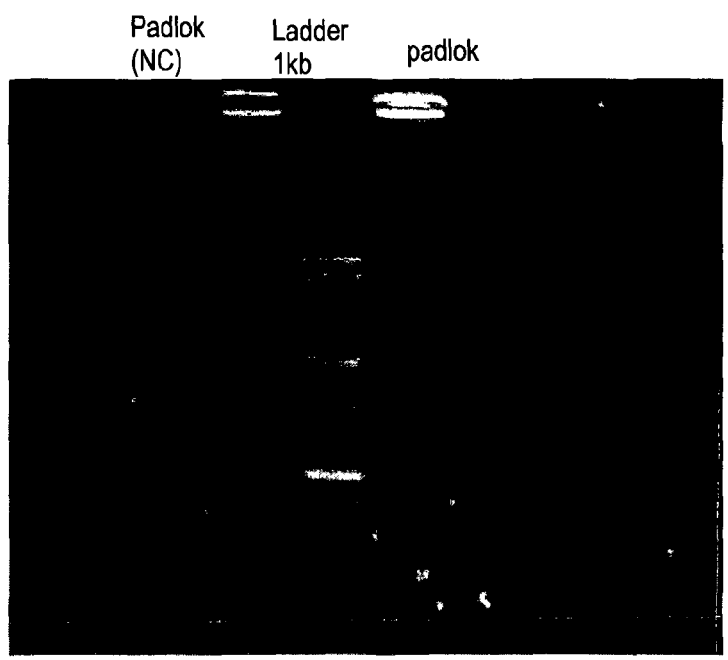
Fig. 11A
t= 0 s
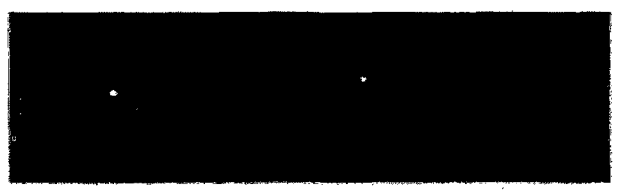
t= 15 s
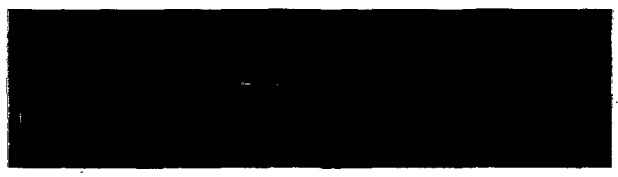
t= 30 s
t= 90 s
(channel depleted in DNA)
Fig. 11B

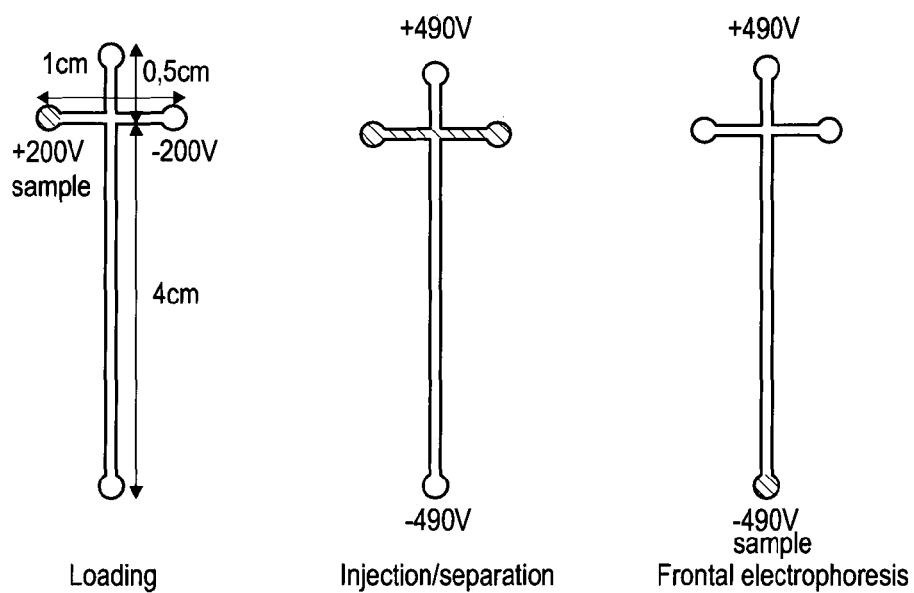
Fig. 12
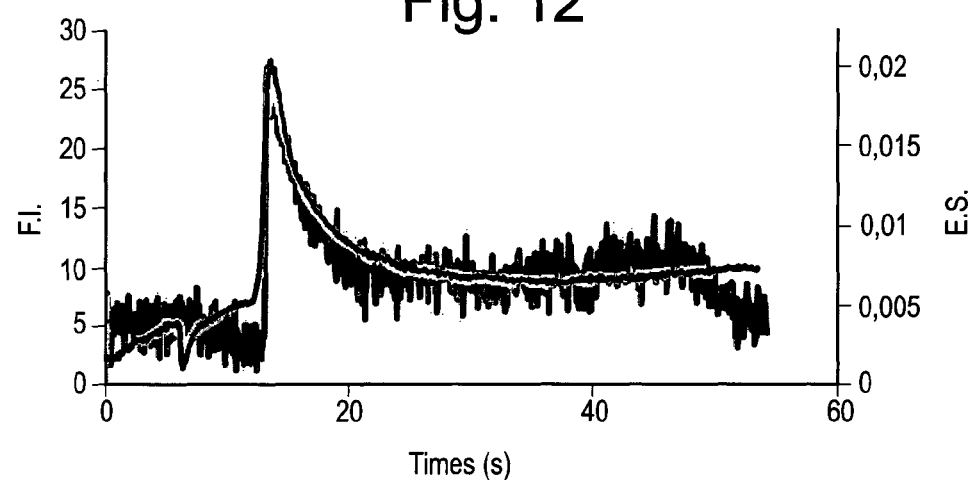
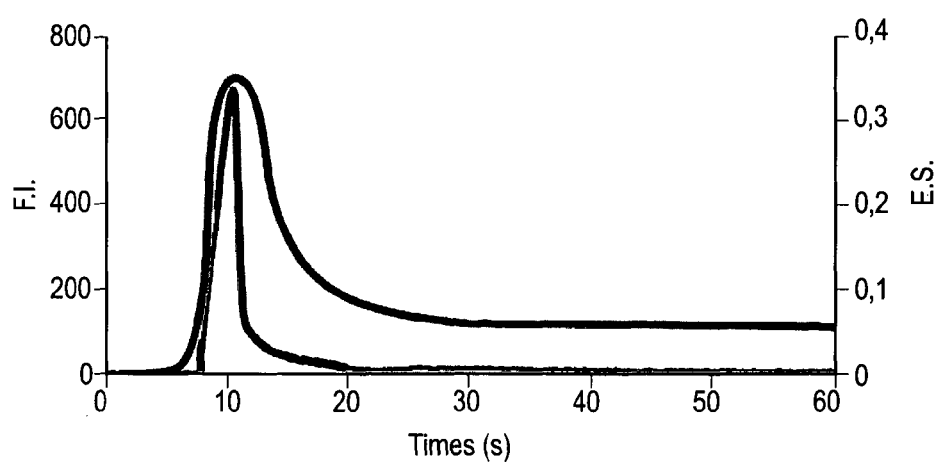
Fig. 13

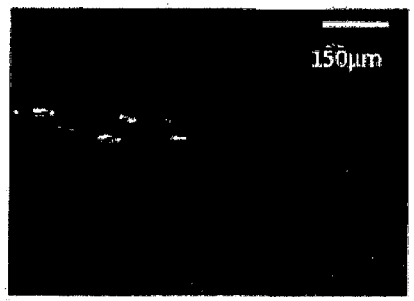 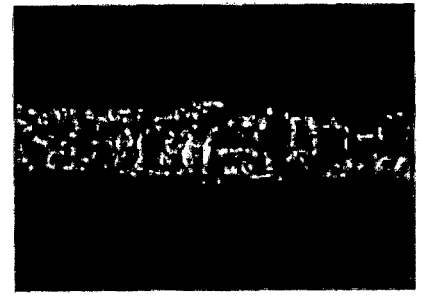
Fig. 16A                    Fig. 16B
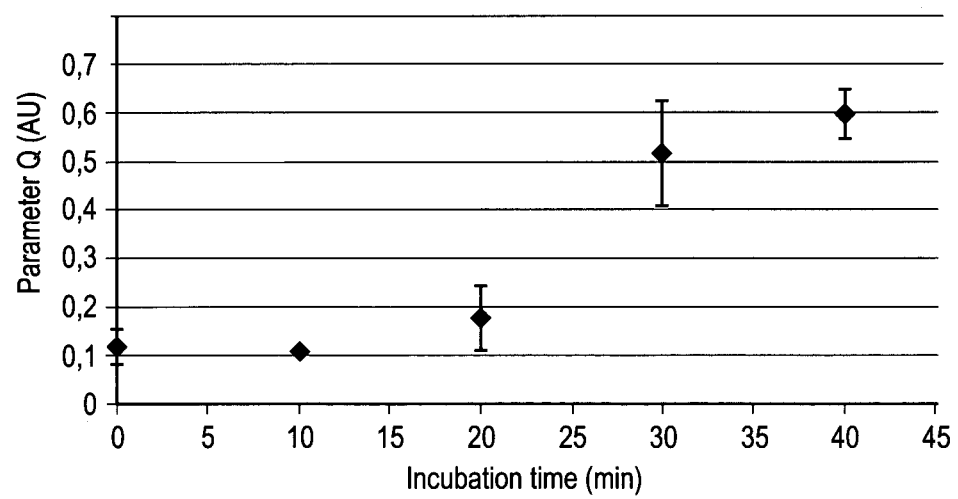
Fig. 17

METHOD AND DEVICES FOR DETECTING MACROIONS IN A LIQUID MEDIUM

The present invention concerns methods and devices for detecting macroions in a liquid medium.

BACKGROUND

Sequence-specific detection of very low quantities of DNA or RNA is useful for a wide range of applications, including clinical diagnostics, food safety testing, forensics, or environmental microbiology.

More generally, most biological species of interest, notably proteins, polysaccharides, nucleic acids, phospholipids, and the combination of such, are charged in solution, and thus constitute ions or most often macroions, meaning they bear a multiplicity of charges. This is also true for numerous colloids or cells or organelles, including, in a non-exhaustive way, viruses, cell nuclei, endosomes, exosomes, mitochondria, bacteria, vesicles. Macroions are also often encountered in chemistry, e.g. as latexes, colloids, nano or microparticles, nanorods, fibers, charged polymer, polyelectrolytes, vesicles, micelles. The charge of these species may be a convenient way to detect said species, since it is an intrinsic property of said species, and does not impose an additional step of labeling.

Charge may be used as a means to separate species, like in the known methods of electrophoresis, electrochromatography or isotachophoresis. However, the known charge-based methods of species detection may not be very sensitive and may also lack specificity, since biological or chemical buffers also contain in general numerous small ions which create a high conductivity background.

Enzymatic amplification methods have provided a tremendous potential in sensitivity, and Polymerase Chain Reaction (PCR) in particular, has become a major and routine tool for genetic analysis.

Numerous systems now exist, from benchtop machines costing a few thousands of €, to more elaborate and high throughput quantitative PCR machines costing several tens of k€. Most of these systems, however, use fluorescence-based detection, and remain dependent on electric power supply from the mains.

Important applications, regarding e.g. pathogen detection in remote environments, biosafety or forensics, would demand portable "point of care" or "point of sampling" assays, and thus efforts over the last decade have been directed in order to integrate this type of assay into microfluidic systems, as described e.g. in A. K. White et al., Proceedings of the National Academy of Sciences, 2011, 108, 2-7.

In order to achieve this, different strategies were proposed which aimed either at reducing the power consumption of fluorescence-based PCR (P. J. Asiello and A. J. Baeumner, Lab on a chip, 2011, 11, 1420-30.) e.g. using diode technologies, or using a DNA equivalent of immuno-agglutination (J. Li, H. Alshammari et al, proc. Microtas 2011, CBMS Publ., pp. 1959-1961, or more radically at avoiding any optics by electrochemistry (see e.g. B. S. Ferguson et al, Analytical chemistry, 2009, 81, 7341-7346.

Fluorescence detectors are so far still unchallenged in terms of sensitivity. However fluorescent detection requires labelling reagents, and developing very low cost technologies, notably for the developing world, is still challenging (see e.g. P. Yager et al., Nature, 2006, 442, 412-8.).

It would thus be very interesting to provide methods able to detect and monitor nucleic acid amplification, and more generally, macroions of biological, medical, environmental, forensic, or chemical interest, without using labels or costly detection techniques. Unfortunately, this is not possible in the state of the art, because the amplification of nucleic acids does not change the global conductivity of a solution. Some electrochemical methods exist, as recited e.g. in Deféver T et al, J Am Chem Soc. 2009 Aug. 19; 131(32):11433-41, but they require labels. It is thus a first object of the invention, to provide a method to detect microions, and particularly to monitor the amplification of nucleic acids, without label and with direct electric read, e.g. conductimetric.

In addition, the conventional methods of quantitative PCR can only be applied to relatively short fragments (less than 2 kbp (see e.g: M. Stegger et al., Clinical Microbiology and Infection, 18: 395-400. doi: 10.1111/j.1469-0691.2011.03715.x). A number of new amplification methods increasingly used in research, including long range PCR (e.g. O. Harismendy et al., Genome biology, 2009, 10, R32), or isothermal amplification produce long nucleic acids fragments. A non-exhaustive list of nucleic acid amplification methods are reviewed and listed e.g. in A. Niemz et al; Trends in Biotechnology, May 2011, Vol. 29, No. 5, pp 240-250. However, these new methods are seldom used in diagnosis or routine, because either of their complexity, or their lack of quantitativeness.

Large nucleic acid molecules can also be analyzed by electrophoresis. The well-known method used to separate large nucleic acids is pulse-field electrophoresis in gels, as described e.g. in WO8402001 to Schwartz and Cantor. This method, however, is very time consuming, e.g., typically 24 hours for a separation, labor intensive, and requires a lot of material.

Attempts have been made to transpose this to capillary electrophoresis, but as shown in Mitnik et al. Science, 1995, 267, 5195, 219-22, high electric fields applied to macroions solutions in capillary lead to another electrokinetic phenomenon, different from the normal transport of ions along field lines. This phenomenon is a nonlinear electrohydrodynamic instability, which gathers DNA into aggregates, creates a lot of noise and ruins separation. This phenomenon is highly non-linear, and its inception depends on field frequency, field strength, and on the concentration and size of the nucleic acid.

Attempts using amphoteric buffers to suppress these aggregates, which is for capillary electrophoresis a strong nuisance, have been proposed e.g. in Magnusdottir et al. Biopolymers, 49, 385-401, (1999) but even then the electric field has to be decreased as compared to conventional capillary electrophoresis, and separation times are too long.

Besides this limitation, capillary electrophoresis systems generally use optical detection methods, either based on UV absorption, or on Laser Induced Fluorescence (LIF), which are expensive, bulky and have a large power consumption. Therefore, attempts have been made to replace these detection methods by direct conductivity detection, since the species separated in electrophoresis are in general, charged.

Numerous methods for conductivity detection, notably in the context of electrokinetic separation and analysis methods, such as capillary electrophoresis, microchannel electrophoresis, or isotachophoresis, have been proposed in the literature.

Reviews can be found for instance in V. Solinova et al., J. Sep. Sci. 2006, 29, 1743-1762 and R. M. Guijt et al., Electrophoresis 2004, 25, 4032-4057. Conductivity detection requires at least two electrodes, in electric connection with the medium under study. Typically, conductivity detection can be implemented in two different families, contact detection, in which the electrodes are in direct electric connection, meaning that they can conduct through the solution continuous or alternating current, or contactless detection, in which said electrodes are in electric relation with the solution through a dielectric layer, so that it can conduct only or mainly alternating current. Contactless conductivity measurements rely on high excitation frequencies (typically in the kHz or MHz range) and capacitive coupling between the electrodes and the solution. The frequency at which conduction occurs typically depends on the thickness of the dielectric layer. This method has the advantage of placing the electrodes outside of the solution through a dielectric, minimizing interferences from the (DC) high electric field, and ground loops. For moderately to highly conductive solutions, however, it is limited in sensitivity, because the impedance of the dielectric layer is high as compared to that of the solution. In addition, the high excitation frequencies required to keep the dielectric's impedance at a reasonable value lead to more expensive and bulky instrumentation.

Contact conductivity measurements uses electrode-solution contact to make measurements of the solution conductivity. This approach is more sensitive than contactless detection, but in methods involving a strong electric fields for moving the species of interest, and notably in capillary electrophoresis, microchannel electrophoresis, it is prone to interactions between the separation field and the detection electronics, resulting in unwanted electrochemical reactions, electrolysis of water, bubble formation and increased noise. To avoid this, Prest et al., in Analyst, 2002, 127, 1413-1419, propose a contact based detection, but they need to have the measurement electrodes in separate vials distant from the separation channel, which reduces the sensitivity. Mo et al., Anal. Commun, 1998, 35, 365-367, also discloses a system, in which electric insulation is performed by an optocoupler, but all these electronic systems have some leaks, and the sensitivity remains low, in the mM range.

Documents MILES US 2002/0070114 and US 2005/0136466 and BRYNING US 2010/0203580 are also known which teach detection methods wherein an analyte is trapped in an electric field.

There are thus needs to improve the sensitivity of conductimetric detection in the presence of an external stimulating field. A need also exists to obtain a low-cost, portable detection technology, notably for analytes at low concentrations, allowing evolution from a "chip in the lab" to a "lab on a chip" paradigm.

A need also exists for a label-free direct-reading of the presence of macroions in a solution, preferably nucleic acids and notably DNA as such as obtained with new amplification methods.

A need also exists to provide a label-free method to detect macroions, and in particular to monitor the amplification of nucleic acids.

A need also exists to obtain a new, simple and low cost electronic device, able to ensure satisfying contact conductivity measurement in microchips with high sensitivity even when a relatively conductive buffer and high external stimulating field are used.

The present invention aims to meet one or more of the aforementioned needs.

SUMMARY

Some objects and features of the present invention are defined in the claims.

According to a first aspect, the present invention relates to a method of detecting macroions in a liquid medium contained in a space, said method comprising:
a) submitting the liquid medium to a stimulating electrical field to induce formation of aggregates of macroions, the formed aggregates of macroions preferably not comprising any additional labeling agent, and
b) measuring, in a detection zone of the space, spatial and/or temporal fluctuations within the liquid medium of at least one variable depending on the concentration of said macroions in the liquid medium, and
c) determining, based on these fluctuations, the presence of the macroions.

By "additional labeling agent", it is meant an additional luminescent, in particular fluorescent, labeling agent.

In a preferred embodiment, the invention uses formation of aggregates by an electrohydrodynamic instability phenomenon, which has so far been considered as a nuisance (see e.g. Magnusdottir et al. Biopolymers, 49, 385-401, (1999)) to perform detection of macroions, in particular to detect nucleic acids or monitor nucleic acids amplification.

The invention advantageously provides low-cost methods for end-point detection of nucleic acids amplification, reaching in some cases a sensitivity better than 100 fg/µl. It also advantageously provides low cost methods for real-time and/or quantitative monitoring of nucleic acids amplification. The invention also advantageously provides low-cost methods for the detection of macroions, notably biological macroions, notably for biological, medical, environmental, forensic, chemical or safety applications.

Preferably, the macroions are polyelectrolytes and aggregates of polyelectrolytes are formed at step a), the polyelectrolytes preferably comprising nucleic acid, more preferably nucleic acid strands having 5 kilo bases or more, or 5 kilobase pairs or more, preferably 10 kilo bases or more or 10 kilobase pairs or more, and nucleic acid aggregates being preferably formed at step a).

The invention enables detection of macroions and monitoring of the production of macroions without using any additional labeling agent thus providing a relatively low-cost method.

In a preferred embodiment, the nucleic acids, in particular the DNA, to be aggregated and detected comprise an intercalating agent, in particular a DNA intercalating agent.

An intercalating agent corresponds to a compound, in particular a molecule, that can insert between the nucleotides constituting a nucleic acid.

The use of an intercalating agent advantageously increases the rigidity of the nucleic acids and facilitates the obtaining of aggregates. This advantageously provides a better sensibility to the detection method according to the invention.

The intercalating agent may be fluorescent, but preferably, the intercalating agent is non-luminescent, in particular non-fluorescent.

The intercalating agent may, non limitatively, be chosen among the following list: Ethidium bromide, SYBR Green I, SYTO-9, SYTO-13, SYTO-16, SYTO-60, SYTO-62, SYTO-64, SYTO-82, POPO-3, TOTO-3, BOBO-3, PO-PRO-3, TO-PRO-3, YO-PRO-1, SYTOX Orange (provided by Life Technologies), QuantiFluor dsDNA system (provided by Promega), Quant-iT PicoGreen (provided by Life Technologies), AccueBlue (provided by Biotium), DAPI (provided by Life Technologies), Hoechst 33258, Hoechst 33342, Hoechst 34580 (provided by Life Technologies), intercalating agents cited in https://en.wikipedia.org/wiki/

Intercalation_(chemistry) the content of which is incorporated by reference, and mixtures thereof.

The ratio (mass of intercalating agent to mass of DNA to be aggregated and detected) may be comprised between 1000 and 0.01, preferably between 100 and 0.1. For high affinity intercalating agents, such a for instance TOTO or YOYO, it is preferably comprised between 20 and 0.1 (see for instance MA Marino et al., Anal Chem, 1998 70, 4514-9), for intercalating agents with less affinity, such as ethidium bromide, propridium iodide, it is more generally comprised between 100 and 1.

The concentration of the intercalating agent in the liquid medium during all or part of step a) may be comprised between 0.01 µmol/l and 200 µmol/l, preferably between 0.1 µmol/l and 10 µmol/l (see e.g. G. T. Irons et al, Cytometry, 15:129 (1994)) or between 1000 µg/ml and 0.01 µg/ml, preferably between 100 µg/ml and 0.1 µg/ml (see e.g. Biorad instructions: http://www.bio-rad.com/webroot/web/pdf/lsr/literature/4006020b.pdf the content of which is incorporated by reference).

As it will be hereunder detailed, the nucleic acids present in the liquid medium at step a) may be obtained after a step of nucleic acid amplification, and the intercalating agent may be introduced in the liquid medium after said step of nucleic acid amplification. In a variant, the intercalating agent can be present in the medium comprising the nucleic acids during the step of nucleic acid amplification.

The spatial and/or temporal fluctuations measured at step b) are preferably non-periodic. The spatial and/or temporal fluctuations measured at step b) are preferably random.

Preferably, the temporal fluctuations within the liquid medium of at least one variable depending on the concentration of the macroions in the liquid medium are measured at step b).

The spatial and/or temporal fluctuations measured at step b) are preferably those of an electrical variable, preferably conductivity or impedance, complex impedance, complex conductivity, current or voltage, more preferably conductivity.

For the sake of terseness, the term "conductivity" shall encompass all different variants of detection of the ability of a medium to transport current, i.e. ohmic conductivity, impedance, complex conductivity, or complex impedance.

The measure may be performed by electrical detection means, examples of said electrical detection means being described below.

In a family of preferred embodiments, the fluctuations of the electrical variable are measured at step b) by at least two electrodes facing each other, along an axis that is transverse, preferably perpendicular, to a direction of the stimulating electrical field.

Preferably, the stimulating electrical field, applied at step a), is applied by electrodes that are different from the electrodes that measure the fluctuations of the electrical variable at step b).

Conductivity measurements are particularly preferred. Indeed, conductivity measurements are universal, low-cost and compatible with direct electronic detection, thus making it easy to miniaturize and integrate.

In a variant, the spatial and/or temporal fluctuations measured at step b) are those of an optical variable, preferably chosen among: optical absorbance, fluorescence, luminescence, dichroism, birefringence, light scattering or optical rotary power.

Step c) preferably comprises processing by a time-dependent or space dependent analysis, preferably by wavelet analysis, or by autocorrelation, the fluctuations measured at step b).

The methods according to the invention allow greater sensitivity to the size of the macroions than the prior art quantitative nucleic acid amplification methods.

Thus, according to another aspect, the present invention also relates to a method for monitoring in real-time the amplification of a nucleic acid comprising:
submitting a nucleic acid to a step of nucleic acid amplification,
submitting the nucleic acid obtained after said amplification or during said amplification to a detection method as described above to obtain a result of detection, and
providing, as a function of the result of detection, information on the level of amplification of the nucleic acid, or information on the initial concentration of the nucleic acid.

The nucleic acid obtained by said amplification preferably comprises nucleic acid strands having 5 kilo bases or more, or 5 kilobase pairs or more, preferably 10 kilo bases or more, or 10 kilobase pairs or more.

The method for monitoring in real-time the amplification of a nucleic acid described above preferably further includes quantifying, from a measured rate of production of large nucleic acids, the initial concentration of nucleic acid in a sample submitted to amplification.

By "large nucleic acids", it is meant nucleic acids having 5 kilo bases or more, or 5 kilo base pairs or more.

The invention also provides devices particularly useful for implementing the methods according to the invention.

According to another aspect, the present invention concerns a conductivity or impedance detector, in particular for carrying out a method according to the invention, or in particular to be used in combination with a stimulating electrical field generator to induce formation of macroion aggregates from a macroion dispersion in the liquid medium or displacement of ions in a ion dispersion, comprising:
a space to receive a liquid medium, the space preferably comprising a liquid medium which contains macroions, preferably polyelectrolytes,
at least two electrodes, said electrodes being:
i. in direct or indirect electric connection, preferably in direct electric connection, with the liquid medium, and
ii. connected to an input of a differential amplifier and to a constant current source through a corresponding resistor.

According to another aspect, the present invention concerns a device, in particular for carrying out the method of the invention, comprising:
a space to receive a liquid medium, the space preferably comprising a liquid medium which contains a plurality of macroions, preferably polyelectrolyte,
at least two electrodes for generating a stimulating electrical field to induce formation of macroion aggregates from a macroion dispersion in the liquid medium, said pair of electrodes being connected to a power supply,
a detector of an electrical variable, preferably a conductivity or impedance detector, comprising a plurality of electrodes to measure spatial and/or temporal fluctuations of the electrical variable induced by the presence of the macroion aggregates in the liquid medium, said plurality of electrodes being identical to or different from the electrodes for generating the stimulating electrical field.

Preferably, the electrodes of the detector are configured to be in contact with the liquid medium. In a variant, they are not.

Two electrodes may be respectively connected to the inverting and non-inverting inputs of a differential amplifier, each electrode preferably being connected to a respective input of the differential amplifier and to a constant current source through a corresponding resistor.

It is also another object of the invention to propose a device, in particular for carrying out the method of the invention comprising:
- a space to receive a liquid medium, the space preferably comprising the liquid medium which contains a plurality of macroions, preferably polyelectrolytes,
- at least two electrodes for generating a stimulating electrical field to induce formation of macroion aggregates from a macroion dispersion in the liquid medium, said pair of electrodes being connected to a power supply,
- a detector of an optical variable, able to measure spatial and/or temporal fluctuations of an optical property affected by the presence of the macroion aggregates in the liquid medium, said optical property being chosen among luminescence or fluorescence intensity, light absorption, light polarization, birefringence, rotary power, preferably light absorption, birefringence or rotary power.

The invention provides a DNA detector, for simple, low cost, possibly portable applications in life sciences, pharmaceutical research, diagnosis, point of care, forensics, biosecurity, environment or food industry.

In another of its aspects, the invention also relates to a device for separating and detecting species, said separation being achieved by an electrokinetic process, and said detection is achieved by one of the devices describe above. In particular, the invention provides detectors for capillary electrophoresis with improved sensitivity and allowing analysis of small ions.

The invention provides low-cost, simple and portable detectors.

The invention provides a device, able to ensure high sensitivity contact conductivity measurements in microchips, while maintaining an excellent electrical decoupling between the stimulating electrical field and the detection device.

The invention also relates to a conductivity or impedance detector, in particular for carrying out a method of the invention in particular to be used in combination with a stimulating electrical field generator to induce displacement of ions in a ion dispersion, and preferably the formation of macroion aggregates from a macroion dispersion in the liquid medium or comprising:
- a space to receive a liquid medium, the space preferably comprising a liquid medium which contains ions, preferably macroions, preferably polyelectrolytes,
- at least two electrodes, said electrodes being:
  i. in direct or indirect electric connection, preferably in direct electric connection, with the liquid medium, and
  ii. respectively connected to the inverting and non-inverting inputs of a differential amplifier.

In another of its aspects, the invention also concerns a method for separating species in a liquid medium contained in a space comprising:
- separating the species by applying a stimulating electrical field using a device and
- measuring, in the detection zone, variations of the impedance or conductivity using a device of the invention comprising:
  at least two electrodes, said electrodes being:
    i. in direct or indirect electric connection, preferably in direct electric connection, with the liquid medium, and
    ii. connected to an input of a differential amplifier and to a constant current source through a corresponding resistor.

A further object of the present invention is a device comprising:
a) a space to receive a liquid medium,
b) an electrical field generator comprising:
   i. a first power supply, and
   ii. a pair of electrodes connected to the first power supply for generating a first stimulating electrical field in the liquid medium, and
c) a detector of an electrical variable to measure, in a detection zone, variations within the liquid medium of the electrical variable, the detector being connected to a second power supply having no common potential reference with the first power supply.

A further object of the present invention is a device, in particular for carrying out the method comprising:
- a space to receive a liquid medium, the space preferably comprising a liquid medium which contains a plurality of macroion, preferably polyelectrolyte,
- at least two electrodes for generating a stimulating electrical field to induce formation of macroion aggregates from a macroion dispersion in the liquid medium, said pair of electrodes being connected to a power supply,
- an optical detector preferably an imaging detector, a camera, or an integrative optical detector.

Preferably, the device further comprises a digital processor to perform a time-dependent or a space dependent analysis, preferably wavelet analysis, or an autocorrelation on the variations of the electrical variable or on the image issued from an imaging detector, or on the output of an integrative optical detector.

A further object of the present invention is a method of detecting charged species in a liquid medium contained in a space comprising:
- using a device as defined above to measure, in the detection zone, variations of the electrical variable, or variations of the output of an integrative optical detector, or spatial fluctuations of the intensity of the image issued from an imaging detector.
- determining, based on these variations, the presence of the charged species, and preferably the charged species concentration in the liquid medium, preferably by processing by a time-dependent or space dependent analysis, preferably by wavelet analysis, or by autocorrelation analysis of the said variations.

A further object of the present invention is a method for separating species in a liquid medium contained in a space comprising:
a) separating the species by applying a stimulating electrical field, and
b) measuring, in the detection zone, variations of the impedance or conductivity using a device of the invention.

A further object of the present invention is a buffer solution configured for being used in a RCA and/or HRCA amplification method in view of carrying out a method as defined above, the solution comprising a polymerase active at a temperature of 37° C. or less, preferably of 30° C. or less, and the solution having a conductivity less than or equal to 1000 mS/m, preferably less than or equal to 500 mS/m, more preferably less than or equal to 350 mS/m, in particular less than or equal to 300 mS/m, in particular less than or equal to 275 mS/m.

In an advantageous embodiment, the liquid medium comprising the macroions to be aggregated used in the method of detecting macroions according to the invention comprises a buffer solution according to the invention.

The use of a buffer solution having a high conductivity may complicate the carrying out of methods of detecting macroions according to the invention since an electrolysis phenomenon may in this case take place near the stimulating electrodes.

As such, using a low conductivity buffer solution according to the invention advantageously allows limiting the electrolysis phenomenon and thus simplifies the detection of the macroions.

In an advantageous embodiment, the buffer solution is used as a buffer solution during a preliminary amplification method, preferably an RCA or an HRCA amplification method, that allows the obtaining of nucleic acids which are to be aggregated during step a) of the method of detection according to the invention.

In another advantageous embodiment, the buffer solution is used as a buffer solution in both the preliminary amplification method and in the liquid medium comprising the nucleic acids to be aggregated used in the method of detection according to the invention.

The buffer solutions according to the invention advantageously simplify the methods according to the invention. Indeed, when using the buffer solutions according to the invention, a desionization step between the preliminary amplification method and the detection of the macroions is not necessary to limit the electrolysis phenomenon.

Preferably, the buffer solution further comprises a ligase.

The use of such buffer solutions e.g. in preliminary RCA or HRCA amplification methods advantageously allows to use a same buffer solution for ligation and amplification steps and thus to carry out these two steps simultaneously.

The polymerase may be a DNA or RNA polymerase.

In a particular embodiment of the invention, the polymerase is chosen among the following list: AmpliTaq, Phi29, different types of "Pol", in particular Pol I, Pol II, Pol III, Pol IV, Pol V, Pol B, Pol alpha, Pol delta, Pol epsilon, Pol kappa, Pol iota, Pol beta, Pol sigma, Pol lambda, Pol mu, different bacteriophage polymerases e.g. polymerase of bacteriophage T4, polymerase of bacteriophage T7, Taq polymerase and its different variants obtained by mutagenesis (see e.g. https://en.wikipedia.org/wiki/DNA_polymerase which is incorporated by reference) and mixtures thereof.

In a particular embodiment, the polymerase is not active at a temperature greater than 80° C., preferably greater than 60° C.

In a particular embodiment of the invention, the ligase is chosen among the following list: T4 DNA Ligase (e.g. provided by Epicentre (Illumina company), New England Biolab (NEB), Promega, Life Technologies, ThermoScientific), Ampligase (e.g. provided by Epicentre (Illumina company)), CircLigase ssDNA ligase (e.g. provided by Epicentre (Illumina company)), CircLigase II ssDNA Ligase (e.g. provided by Epicentre (Illumina company)), E. Coli DNA Ligase (e.g. provided by Epicentre (Illumina company)), Taq DNA Ligase (e.g. provided by New England Biolab (NEB), Life Technologies), T3 DNA Ligase (e.g. provided by New England Biolab (NEB)), T7 DNA Ligase (e.g. provided by New England Biolab (NEB)), 9° NTM DNA Ligase (e.g. provided by New England Biolab (NEB)) and mixtures thereof. A further object of the present invention is a method of detecting macroions in a liquid medium contained in a space, said method comprising:

a) submitting the liquid medium to a stimulating electrical field to induce formation of aggregates of macroions and displacement of said macroion aggregates in the liquid medium, the formed aggregates of macroions preferably not comprising any additional labeling agent, and b) measuring, in a detection zone of the space, spatial and/or temporal fluctuations within the liquid medium of at least one variable depending on the concentration of said macroions in the liquid medium, and c) determining, based on these fluctuations, the presence of the macroions, step c) preferably comprising processing by a time-dependent or space dependent analysis, more preferably by wavelet analysis, or by autocorrelation the fluctuations measured at step b).

Preferably, the variable is electrical, the fluctuations of the electrical variable being measured at step b) by at least two electrodes in direct electric contact with the liquid medium, and the aggregates are caused to displace relatively to the electrodes during all or part of step b).

A further object of the present invention is a method of detecting nucleic acids in a liquid medium contained in a space, said method comprising:

a) submitting the liquid medium to a stimulating electrical field to induce formation of aggregates of nucleic acids, the nucleic acids comprising nucleic acid strands having 50 kilo bases or more or 50 kilobase pairs or more, the formed aggregates of nucleic acids preferably not comprising any additional labeling agent, and b) measuring, in a detection zone of the space, spatial and/or temporal fluctuations within the liquid medium of at least one variable depending on the concentration of said nucleic acids in the liquid medium, and c) determining, based on these fluctuations, the presence of the nucleic acids, step c) preferably comprising processing by a time-dependent or space dependent analysis, more preferably by wavelet analysis, or by autocorrelation the fluctuations measured at step b).

Macroions

One or a plurality of types of macroions may be present in the liquid medium. Macroions are typically objects bearing a multiplicity of charges, preferably more than 10 charges per object.

Macroions may comprise or be deprived of an additional labeling agent. Preferably, said macroions do not comprise any additional labeling agent.

Thus, the macroions may have properties that can be intrinsic or imparted by an additional labelling agent.

The additional labelling agent may be chosen among the following list: SYBR Green I, SYTO-9, SYTO-13, SYTO-16, SYTO-60, SYTO-62, SYTO-64, SYTO-82, POPO-3, TOTO-3, BOBO-3, PO-PRO-3, TO-PRO-3, YO-PRO-1, SYTOX Orange (provided by Life Technologies), QuantiFluor dsDNA system (provided by Promega), Quant-iT PicoGreen (provided by Life Technologies), AccueBlue (provided by Biotium), DAPI (provided by Life Technologies), Hoechst 33258, Hoechst 33342, Hoechst 34580 (provided by Life Technologies) and mixtures thereof.

The concentration of the additional labelling agent in the liquid medium during all or part of step a) may be comprised between 0.01 µmol/l and 200 µmol/l, preferably between 0.1 µmol/l and 10 µmol/l (see e.g. G. T. Irons et al, Cytometry, 15:129 (1994)) or between 1000 µg/ml and 0.01 µg/ml, preferably between 100 µg/ml and 0.1 µg/ml (see e.g. Biorad instructions: http://www.bio-rad.com/webroot/web/pdf/lsr/literature/4006020b.pdf the content of which is incorporated by reference).

All optical quantities related with the concentration of macroions, such as e.g. optical absorbance, fluorescence, luminescence, dichroism, birefringence optical rotary power, or light scattering, and preferably fluctuations of said properties induced by a stimulating electric field, can be used in the invention, provided spatial fluctuations of said properties can be recorded by some detection means, preferably optical means.

All electric or dielectric or electromagnetic properties related with the concentration of macroions, such as e.g. charge, pI, conductivity, electrophoretic mobility, polarizability, magnetic moment, and preferably fluctuations of said properties induced by a stimulating electric field, can be used in the invention, provided spatial fluctuations of said properties can be recorded by some detection means, preferably electrical means The macroions may be polyelectrolytes, charged colloids, or nanoparticles.

By "colloids", it is meant objects which have an average size comprised between 50 nm and 100 µm when isolated (i.e. not aggregated), preferably between 50 nm and 10 µm. Nanoparticles are typically particles ranging from 2 nm to 100 nm.

By "average size", it is meant the statistical granulometric dimension at the half of the population, known as D50.

As used herein, the term "colloidal object" may represent a large variety of natural or artificial, organic, or inorganic, compounds, including cells, organelles, viruses, cell aggregates, cell islets, embryos, pollen grains, artificial or natural organic particles such as latex particles, dendrimers, vesicles, magnetic particles, nanoparticles, quantum dots, metal microparticles, metal nanoparticles, organometallic micro or nanoparticles, nanotubes, artificial or natural macromolecules, microgels, macromolecular aggregates, proteins or protein aggregates, polynucleotides or polynucleotide aggregates, nucleoproteic aggregates, polysaccharides, or supramolecular assemblies, or combinations of the hereabove compounds.

The term "particle" will be used in the description with the same meaning as "colloidal object".

As used here, the term "colloidal fluid" or "colloidal suspension", refers to a fluid containing colloidal objects.

Polyelectrolytes and Nucleic Acids

Polyelectrolytes are charged macromolecules. In some cases, the charges in said polyelectrolytes may have a weak acid or basic character, and can thus be un-charged in some conditions of pH. They are nevertheless considered as polyelectrolytes in the invention, as long as they can bear a charge in some solvents and pH or buffer conditions.

The invention is particularly advantageous for analyzing nucleic acids. Said nucleic acids can be single stranded or double stranded DNA, RNA, messenger RNA, microRNA, interferent RNA, natural or artificial oligonucleotides, and also encompass all kinds of natural or artificial nucleic acids, such as and non limitatively, phosphorylated or methylated DNA or RNA, LNA, PNA, fluorescently labeled DNA or oligonucleotides.

In other preferred embodiments, polyelectrolytes in the invention may be proteins, polypeptides, polysaccharides, oligosaccharides, glycoproteins, phospholipids, lipids, and their modifications, e.g. and non limitatively, by phosphorylation, methylation, glycosylation.

The polyelectrolytes present in the liquid medium at step a) may be obtained after or during a step of nucleic acid amplification, said amplification preferably being a real-time quantitative amplification or comprising at least one of: a Reverse transcription, a Polymerase Chain Reaction amplification, an isothermal nucleic acid amplification, a rolling circle amplification, a branched rolling circle amplification, a circle to circle amplification, a LAMP (loop-mediated amplification), NASBA (nucleic acid sequence-based amplification) TMA (Transcription-mediated amplification), SMART (Signal-mediated amplification of RNA technology), HDA (Helicase-dependent amplification), RPA (recombinase polymerase amplification), CPA (Cross-priming amplification), SMART-AMP (Smart amplification), RCA (Rolling-Circle Amplification), HRCA (Hyperbranched Rolling-Circle Amplification), RAM (ramification amplification), SDA (strand displacement amplification), NEAR (Nicking enzyme amplification reaction), NEMA (Nicking enzyme-mediated amplification), ICA (Isothermal chain amplification), EXPAR (Exponential amplification reaction), BAD AMP (Beacon-assisted detection amplification), or nucleic acid amplification methods using Phi29 DNA polymerase.

The carrying out of an HRCA amplification method is advantageous since this method selectively and quickly amplifies DNA.

Amplification

The invention is particularly interesting for monitoring the amplification of nucleic acids, and thus in combination with methods for amplifying nucleic acids, notably, as a non limitative list, Reverse transcription, a Polymerase Chain Reaction amplification, an isothermal nucleic acid amplification, a rolling circle amplification, a branched rolling circle amplification, a circle to circle amplification, a LAMP NASBA TMA, SMART, HAD, RPA, CPA, SMART-AMP, RCA, HRCA, RAM, SDA, NEAR, NEMA, ICA, EXPAR, BAD AMP, or PG-RCA amplification, or nucleic acid amplification methods using Phi29 DNA polymerase methods leading to large nucleic acid fragments, such as long-range PCR, RCA, branched RCA, HRCA, C2CA, LAMP, RAM, Smart-AMP, CPA, Smart-AMP. are particularly suitable for the invention.

In a particular embodiment, the nucleic acid is present in a medium comprising a buffer solution during the step of nucleic acid amplification, and the liquid medium used at step a) also comprises the same buffer solution.

In a particular embodiment, the buffer solution has a conductivity less than or equal to 1000 mS/m, preferably less than or equal to 500 mS/m, more preferably less than or equal to 350 mS/m, in particular less than or equal to 300 mS/m, in particular less than or equal to 275 mS/m.

In a particular embodiment, the buffer solution comprises a polymerase active at a temperature of 37° C. or less, preferably of 30° C. or less.

The buffer solution may further comprise a ligase and/or a DNA polymerase.

In a variant, the nucleic acid is present in a medium comprising a first buffer solution during the step of nucleic acid amplification, and the liquid medium used at step a) comprises a second buffer solution, different from the first.

The second buffer solution is preferably less conductive than the first buffer solution. The second buffer solution preferably has a conductivity less than or equal to 1000 mS/m, preferably less than or equal to 500 mS/m, more preferably less than or equal to 350 mS/m, in particular less than or equal to 300 mS/m, in particular less than or equal to 275 mS/m.

The second buffer solution may be obtained after a deionization of the first buffer solution.

Fluidic System

The invention is preferably applied in microfluidic, millifluidic or nanofluidic systems or equivalently, microfluidic devices, because these systems may allow reducing sample and reagent consumption and Joule heating.

As used herein, "microfluidic device" refers to an embodiment comprising microchannels, having at least one of their dimensions of less than 500 microns (micrometers). The same, "millifluidic" device refers to an essentially rigid embodiment comprising at least one millichannel, i.e. a channel with at least one dimension less than 5 mm. The same, "nanofluidic" device refers to an essentially rigid embodiment comprising at least one channel with at least one dimension less than 1 µm. So far, however, microfluidic devices are more extensively used than millifluidic or nanofluidic ones, so for the sake of terseness, except when specifically stated otherwise, we'll encompass in the following description microfluidic, millifluidic or nanofluidic devices under the generic adjective of "microfluidic".

As used herein, we also define as a "microfluidic system" (encompassing, for terseness, also "millifluidic or nanofluidic systems", an ensemble of devices and connecting elements, comprising a microfluidic or a millifludic or nanofluidic device, respectively. Typically, a microfluidic (millifluidic, nanofluidic) system comprises at least a micro fluidic (millifluific, nanofluidic) device, and it may also comprise reservoirs containing samples or reagents, one or several pumping devices in order to actively transfer fluid from said reservoir(s) to said microfluidic (millifluidic, nanofluidic) device, and fluidic connecting elements. Optionally, such fluidic systems may also comprise one or several detectors. Said detectors may be integrated into said fluidic device, or independent.

Optionally, microfluidic systems of the invention may also comprise valves, holders, observation means, and any kinds of fittings usable to keep its different components and devices together.

Optionally, microfluidic systems of the invention may also comprise any kind of computer, electronic, electric or pneumatic controllers, in order, and non limitatively, to control the temperature and functioning of its components, to automate its operation, to record data etc.

Space

The space is preferably defined by a chamber, preferably by a well, e.g. by a well from a microtiter plate, or by a channel, more preferably by a microchannel.

The space may be of various sizes, natures and shapes.

The space preferably has at least one of its dimensions that is smaller than or equal to 1 mm, preferably comprised between 1 µm and 100 µm, particularly preferably between 5 µm and 50 µm.

The invention is advantageously performed in parallel or sequentially, in an array of chambers, preferably microchambers, or in an array of wells, preferably microwells, as e.g. wells of a microter plate, preferably a 96 wells or 384 wells microtiter plate, and more preferably microtiter plates with more than 1000 wells per plate.

At least one wall of the chamber, preferably well, or of the channel, preferably microchannel, defining the space preferably comprises, in particular consists of, a non-conductive material.

At least one wall of the chamber, preferably well, or of the channel, preferably microchannel, defining the space preferably comprises, in particular consists of, a transparent material. The wall thus may comprise a transparent detection window.

The use of such a transparent material is particularly preferred when fluctuations or variations of an optical variable are measured.

Preferably, the space presents an enlargement at the detection zone, the space preferably being defined by a chamber or a channel. The enlargement present at the detection zone advantageously facilitates the alignment of the electrodes in the detection zone.

The enlargement present at the detection zone advantageously facilitates decoupling between the electrodes and the high voltage power supply by decreasing locally the driving field intensity, without significantly affecting aggregate formation.

In a particular embodiment, the space comprises a plurality of detection zones, each of the detection zones comprising a detector of at least one variable depending on the concentration of the macroions in the liquid medium.

In a particular embodiment, the liquid medium comprises different types of macroions, in particular of nucleic acids, to be detected, and compounds configured to interact with the macroions are present in each of the detection zones, the compounds present in one detection zone being different from the compounds present in another detection zone.

In a particular embodiment, the macroions to be detected are nucleic acids and the compounds are configured to interact with, in particular to hybridize to, different nucleotide sequences of said nucleic acids.

In a particular embodiment, the space is elongated along a longitudinal axis and the detection zones succeed each other along the longitudinal axis.

In a particular embodiment, the space comprises a plurality of sub-channels each comprising a detection zone.

In a particular embodiment, the spatial and/or temporal fluctuations within the liquid medium of at least one variable depending on the concentration of said macroions in the liquid medium are measured simultaneously among each of the detection zones.

In a particular embodiment, the spatial and/or temporal fluctuations within the liquid medium of at least one variable depending on the concentration of said macroions in the liquid medium are measured sequentially among each of the detection zones.

In a particular embodiment, the spatial and/or temporal fluctuations within the liquid medium of at least one variable depending on the concentration of said macroions in the liquid medium are measured among each of the detection zones and step c) comprises processing said spatial and/or temporal fluctuations measured from the plurality of detection zones.

The use of a plurality of detection zones advantageously allows to detect different macroions, e.g. biomarkers, simultaneously and/or to improve quality of detection since it allows e.g. to correlate the fluctuation signals obtained from the different detection zones.

In a particular embodiment, an average of the fluctuation signals obtained from the different detection zones can be made during step c).

In a particular embodiment, the devices according to the invention comprise a space comprising a plurality of detection zones, each of the detection zones comprising a detector of an electrical and/or of an optical variable depending on the concentration of the macroions in the liquid medium.

In a particular embodiment, the devices according to the invention comprise a space elongated along a longitudinal axis and the detection zones succeeding each other along the longitudinal axis.

In a particular embodiment, the devices according to the invention comprise a space comprising a plurality of sub-channels each comprising a detection zone.

Liquid Medium

The liquid medium may be a biological liquid such as blood or plasma, or serum, urine, pleural effusion, cerebrospinal fluid, or any sample extracted from organisms. In can also be a suspension or resuspension of cells, from living organisms of a culture. Optionally the liquid medium may have been subjected to and kind of pretreatment, such as and non limitatively purification, extraction, centrifufation, filtration, culture, incubation, thermal treatment etc. In preferred embodiment, said liquid comprises a mix for nucleic acid amplification. In preferred embodiments, it may contain one or several of primers, polymerases, ligases, enzymes etc.

In other preferred embodiments, the liquid medium is a suspension of artificial or natural polymers. In other preferred embodiments, it is a suspension of organic, inorganic or combined organic-inorganic colloids, or nanoparticles.

In a variant, the liquid medium may be water, deionized or not, and may contain a pH buffer.

The liquid medium may be transparent to visible light.

The liquid medium may not be flowing during all or part of the methods according to the invention.

According to an embodiment, the liquid medium is flowing during all or part of the methods according to the invention, the Reynolds number of the flow of the liquid medium preferably being less than 10.

Preferably, said liquid medium does not comprise any additional labeling agent.

Aggregates

The macroion aggregates formed from a solution with a uniform concentration c in macroions, typically have a concentration in macroions larger than c and deplete their surroundings from macroions, such surroundings thus having, in the presence of the aggregates, a concentration in macroions smaller than c.

Therefore, aggregate formation creates spatial fluctuations of the concentration in macroions that are significantly larger than the spatial fluctuations in the absence of the stimulating electrical field.

The total concentration of the macroions in the liquid medium is preferably not be modified by the aggregate formation.

Aggregate formation preferably creates random spatial fluctuations of the macroion concentration in the liquid medium.

The aggregates preferably have no specific positioning relatively to the detection electrodes. In particular, the aggregates are not trapped proximate to the electrodes during steps b) and/or c).

The inventors have discovered that, surprisingly and in contrast with prior art as described e.g. in Magnusdottir et al. Biopolymers, Vol. 49, 385-401 (1999) in which these fluctuations prevented DNA analysis, by using the concentration dependence of the onset of this spectacular phenomenon, it was indeed possible to detect DNA, and in particular to monitor DNA amplification without labels, by applying onto a DNA solution a stimulating electric field with suitable properties to yield such aggregates, and then recording the formation of these aggregates.

Measurement of the Aggregates by an Integrative Detection Method

In contrast to known conductivity methods for detecting macroions, the methods of the present invention may not measure average conductivity of the medium but may use the level of aggregation reflected by the fluctuations of a variable, preferably an electrical or optical variable, said fluctuations depending on the concentration of macroions prior to applying a stimulating electric field, and depending on the characteristics of said stimulating electric field.

Observations of aggregates used in the invention, e.g. as in FIG. 8, shows that, when contained in a space, e.g. a chamber or microchannel, they generally take an elongated shape in a direction transverse or tilted with regards to the direction of the stimulating field, until they encounter the space wall, and then keep a roughly constant size.

Also, because of the presence, in general, of a multiplicity of aggregates, and of their random nature, in order to maximize the signal it may be interesting to record the fluctuations of a variable under the action of a stimulating electric field, notably an electric or optical variable, by making a multiplicity of measures of said variable in volume or area elements with a size of the order of the typical size of the aggregates. This way, the amplitude of the signal may comprise in some case the whole of an aggregate, or alternately no aggregate at all.

Therefore, in preferred embodiments, the size of the area A or volume V in which a realization of a signal measurement is done, is of the same order as that of the smallest dimension of the space in which the stimulating field is applied, in a direction perpendicular to said field. In preferred embodiments, it is comprised between 0.1 and 10 times said smallest dimension, preferably between 0.1 and 1 times said smallest dimension. For instance, in some preferred embodiment where the variable is an electric variable, the spacing between the electrodes recording said variable, is preferably comprised between 0.02 and 20 times the smallest dimension of the space in which the stimulating field is applied, in a direction perpendicular to said field, preferably between 0.1 and 10 times said smallest dimension preferably between 0.3 and 3 times said dimension, preferably between 0.3 and 1 times said dimension.

In some preferred embodiment where the variable is an optical variable, and this optical variable is recorded by an integrative photodetector, the size of the observation area of the detector is preferably comprised between 0.02 and 20 times the smallest dimension of the space in which the stimulating field is applied, in a direction perpendicular to said field, preferably between 0.1 and 10 times said smallest dimension, preferably between 0.3 and 3 times said dimension, preferably between 0.3 and 1 times said dimension.

By integrating or integrative photodetector is a photodetector that integrates the light providing from an area or volume of space, and delivers a signal (in general an electric signal) reflecting said integrated light intensity. Typical integrative photodectors are photodiodes, photomultipliers, avalanche photodiodes.

Measurement of the Aggregates by an Imaging Device

In some preferred embodiments, the spatial fluctuations of concentration of macroions can be directly recorded and used for extracting a signal, for instance using an imaging device which takes instantaneous images encompassing many aggregates, and performing a spatial image analysis.

An image of an area of the space, submitted to the excitation electric field is made and recorded. An analysis aimed at extracting fluctuations of light intensity, or of light color, in said area, is then applied. Optionally, as a reference the results of said analysis during or application of said stimulating field can be compared to the results of said analysis before the application of said stimulating electric field, or to a reference value obtained in the absence of the species to detect.

We define imaging devices or imaging photodetector are devices that provide a spatially resolved image of an observed area. Typical imaging photodetectors are conventional tube cameras, argentic cameras, CCD cameras, CMOS cameras, photodiode arrays etc. In a specific embodiment, exemplified in FIG. 8 and example 6, said imaging device is a CCD camera.

In such embodiments comprising an imaging device, the image may be recorded in a volume that is elongated in the direction of the stimulating field, and have a width comparable with the dimension of the chamber or channel in which the field is applied, in a direction perpendicular to said field. Then, multiple aggregates are recorded at the same time, and an image analysis algorithm is used to extract the fluctuations from said image, corresponding to the typical size of the aggregates, as will be explained in more detail below. Preferably, said image analysis algorithm comprises a 2Dimensional wavelet analysis Stimulating Electrical Field
Properties of the Stimulating Electrical Field The features of the stimulating electrical field may vary according to the nature, concentration or size of the macroions, in particular of the DNA target, and to the conducting properties of the liquid medium.

The stimulating electrical field applied at step a) of the method of the invention is preferably:
  a continuous or an alternating electrical field of frequency less than or equal to 1000 Hz, preferably less than or equal to 100 Hz, and/or
  has an intensity greater than or equal to 50 V/cm, preferably greater than or equal to 100V/cm, more preferably greater than or equal to 200 V/cm, and/or
  comprises a superposition of at least a first and a second electrical field components with different frequencies, the second electrical field component having an amplitude that is lower than the amplitude of the first electrical field component and the second electrical field component being either continuous or having a frequency that is lower than the frequency of the first electrical field component.

The intensity of the stimulating electrical field may be measured at the detection zone, or predetermined by imposing potentials on two sides of a space or microchannel, and calculating said field according to Laplace equation. For instance in the case of linear microchannel with constant section, the field amplitude is roughly equal to the imposed electric potential divided by the microchannel length.

The use of a superposition of at least two electrical fields components having different frequencies in the stimulating field advantageously allows forming macroion aggregates and displacing said macroion aggregates in the liquid medium. Typically a first component called the major component has a first amplitude and a first frequency, and a second component, called the bias has a second amplitude smaller than said first amplitude, and a second frequency smaller than said frequency, or is a continuous field component.

This way, the first component of the field creates the aggregates, and the second component drives them across the detection area. Thus, the use of a superposition of two electrical fields components advantageously produces in the detection zone a temporal fluctuation of a variable having a higher fluctuation rate than if only spontaneous displacement of aggregates was used.

This higher fluctuation rate simplifies the statistical analysis of the fluctuations, making it more accurate and allows a faster detection because spontaneous motion of the aggregates may be relatively slow.

The use of such a superposition of two electrical fields is particularly preferred when aggregate formation creates random spatial fluctuations of the macroion concentration in the liquid medium.

More generally, the aggregates can be displaced via a hydrodynamic flow, or more generally thanks to a pressure difference between two points of the space. In this case, only one electrical field may be used to form the aggregates, the displacement of these aggregates being ensured thanks to a pressure difference or a flow.

The fluctuations of the electrical variable are preferably measured at step b) by at least two electrodes polarized by an alternative polarization signal having a frequency that is different from the highest frequency component of the of the stimulating electrical field applied at step a), the frequency of the polarization signal preferably being greater than, more preferably at least 10, more preferably 100, more preferably 1000, times greater than, said frequency component.

Electrodes Generating the Stimulating Electrical Field

In one preferred family of embodiments, the electrodes for generating the electrical field are different from the electrodes used for detection.

In some embodiments the electrodes creating the stimulating field are in the chamber or microchannel containing the solution containing the macroions, and in direct contact with the latter, in other embodiment they are in distinct reservoirs in fluidic connection with the chamber or microchannel. Preferably, they are far apart as compared to the distance between the measurement electrodes.

In another preferred family of embodiments, same electrodes may be used for generating the electrical field and for the detection.

Such a configuration may be advantageous since it allows using a relatively simple device.

Indeed, in such a configuration, a single power source may be required. Further, if the electrodes are close enough, a stimulating electrical field able to induce formation of aggregates of macroions may be generated without requiring a high voltage power supply.

More than two electrodes may be used e.g. 3, 4 or even tens of electrodes.

The electrodes for the generation of the stimulating electrical field may be connected to a circuit comprising one or a plurality of uncoupler(s), preferably isolation amplifier(s), which have a floating ground.

This configuration may advantageously allow reducing interferences between the stimulating electrical field applied and the detection device.

Power Supply for Generating the Stimulating Electrical Field

The power supply used for generating the stimulating electrical field may comprise, in particular may consist of, a balanced circuit. In other words, the power supply may preferably be a symmetric power supply.

The use of a balanced circuit helps reduce the interference.

In some embodiments, the power supply comprises at least one, preferably two, high voltage amplifiers. In other preferred embodiments, the power supply comprises at least one, preferably two, DC to DC voltage converters.

The power supply is preferably operated from standard batteries, for example standard 9V batteries.

Detector
Measurement Electrodes
Configuration of the Electrodes

The fluctuations of the electrical variable is preferably measured at step b) by at least two electrodes in direct electric contact with the liquid medium.

In another embodiment, the fluctuations of the electrical variable are measured at step b) by at least two electrodes in indirect electric connection with the liquid medium through a dielectric layer.

These configurations allow reducing interference between the stimulating electrical field applied and the detection device.

The fluctuations of the electrical variable may also, in some embodiments, be measured at step b) by at least two electrodes located at different positions along an axis parallel to a direction of the electrical field.

Also, the stimulating electrical field, applied at step a), may be applied by the same electrodes as those that measure the fluctuations of the electrical variable at step b).

This way, a single power source is needed, and due to the close proximity of the electrodes, a stimulating electric field high enough to create aggregates can be achieved without the need of a high voltage power supply. However, in this embodiment the aggregates are localized between the electrodes, making a statistical analysis more difficult. To compensate for this, more complex electrode configurations, comprising more than two, e.g., 3, 4 or even tens of electrodes, may be advantageous to recover a good statistical analysis.

In embodiment where the detector comprises at least two electrodes, said detector electrodes are preferably configured to measure the variations of the electrical variable at a location in the liquid medium wherein the absolute value of the electrical potential inducing said stimulating electrical field is minimal, preferably substantially null.

This configuration allows reducing interference between the stimulating electrical field applied and the detection device.

Preferably, the first power supply is a symmetric power supply.

In another preferred embodiment, to be preferred when the first power supply is not a symmetric power supply, the electrodes used to measure the fluctuations or variations of the electrical variable may be located at a location in the liquid medium where the absolute value of the potential generated by the first power supply is substantially equal to, preferably equal to, the potential of the reference of said first power supply.

Preferably, the first power supply is connected to a ground reference. Preferably, said ground reference is also the potential of reference of said power supply. The latter may reduce risks of arcs, unstable potentials and risks for users.

Size of the Electrodes

The detector electrodes preferably have a width less than or equal to 200 µm, preferably less than 100 µm, Electrodes having a relatively low width allow reducing the interference between the stimulating electrical field applied and the detection device.

The dimensions of the detector electrodes and/or their spacing are preferably comprised between 0.1 and 10 times, preferably between 0.3 and 3 times, the largest dimension of the detection zone measured in a direction perpendicular to a direction of the stimulating electrical field.

In a preferred embodiment, the electrodes are coated with at least one layer comprising a surface-treating agent.

The use of such surface-treating agent advantageously allows reducing adsorption of nucleic acids obtained after nucleic acid amplification, e.g. HRCA amplification, on the electrodes.

The surface-treating agent may be a hydrogel or a surfactant.

In a particular embodiment, the surface-treating agent is chosen among the following list: hydrosoluble cellulose derivatives such as hydroxyethyl cellulose, hydroxymethylcellulose, methylcellulose, polyvinyl alcohol, polyvinyl pyrrolidone, acrylic and methacrylic derivatives, substituted or not, such as polydimethyl acrylamide, polydimethyl acrylamide-allyl glycidyl ether polyacrylamide, copolymers obtained from various types of acrylic, alkyl-acrylic, substituted or not, monomers, polyethylene glycol, polypropylene glycol, copolymers of polyethylene and polypropylene glycol, in particular those sold under the commercial name Pluronics®, products of the polymerization of polymers functionalized by acrylic or methacrylic derivatives, polymers, oligomers or molecules, preferably hydrosoluble, having silane functions, polymers, oligomers or molecules, preferably hydrosoluble, having thiols functions, and mixtures thereof.

Optical Detection

Similarly to the above-described embodiments for electrodes, when fluctuations or variations of an optical variable are measured, e.g. using an integrative photodetector, the observation area of the detector preferably has a dimension comprised between 0.1 and 10 times, preferably between 0.3 and 3 times, the largest dimension of the detection zone measured in a direction perpendicular to a direction of the stimulating electrical field.

It can be noted that the signal variations is generally maximal when the whole of an aggregate, but no more than one aggregate, encompasses the detection zone.

Measurement Timing

In some preferred embodiments, fluctuations of the variable are preferably measured while the stimulating electrical field is not applied, the stimulating electrical field, preferably not being applied during first periods, said first periods alternating with second periods during which the stimulating electrical field is applied.

This embodiment is particularly suitable, when the electrodes used to create the stimulating field are the same as the electrodes used to detect conductivity fluctuations.

The fluctuations of concentration may relax relatively rapidly, typically within from 1 to 100 seconds. This relaxation may diminish the amplitude of the measured fluctuations.

Therefore, the periods wherein the stimulating electrical field is not applied preferably have a duration less than or equal to 100 s, preferably 10 s.

In a variant, the fluctuations of the variable are measured while the stimulating electrical field is applied.

In this case, it may be interesting to reduce interference between the stimulating electrical field and the detector using all or part of the solutions described in the present disclosure.

Also, in some embodiments the electric variable is measured at the frequency of polarization of the measuring electrodes, using a filtering that rejects the frequency or the frequency components present in the stimulating electric field. Preferably, too, the polarization frequency of the measuring electrodes is not a multiple of the frequency of the stimulating electric field.

Polarization Signal

Preferably, the fluctuations of the electrical variable are measured at step b) by at least two electrodes polarized by an alternative polarization signal having a frequency that is different from the highest frequency component of the stimulating electrical field applied at step a), the frequency of the polarization signal preferably being greater than, more preferably at least 10, more preferably 100, more preferably 1000, times greater than, said frequency component.

This allows obtaining better decoupling between the stimulating electrical field and the detector.

The frequency of the polarization signal, particularly when the detector electrodes are in contact with the liquid medium, is preferably comprised between 1 kHz and 100 kHz, preferably between 1 kHz and 50 kHz.

The use of such frequencies enables avoidance of electrochemical reactions at the electrode surface and creation of Faraday currents. In the contactless detection mode, said polarization frequency may be comprised between 1 kHz and 100 MHz, preferably between 10 kHz and 50 MHz, more preferably between 100 kHz and 10 MHz.

The frequency of the polarization signal is preferably different from a non-zero multiple of a frequency of the stimulating electrical field.

Electronic Circuit

When the variations or fluctuations of an electrical variable are measured, the detector may comprise detector electrodes and an electronic circuit, said electrodes being connected to the electronic circuit.

The electronic circuit preferably applies the above described polarization signal to the detector electrodes.

The electronic circuit may comprise:
- at least one, preferably two, more preferably three, uncoupler(s), said uncoupler(s) preferably being isolation amplifier(s), and/or
- at least one, preferably at least two, voltage controlled current sources, and/or
- a bridge of resistors, and/or
- a differential amplifier, or any combination of said four types of components.

In a preferred embodiment, the electronic circuit comprises:
- at least one, preferably two, more preferably three, uncoupler(s), said uncoupler(s) preferably being isolation amplifier(s), and
- at least one, preferably at least two, voltage controlled current sources, and
- a bridge of resistors, and
- a differential amplifier.

The use of isolation amplifiers is preferred because isolation amplifiers notably have the advantage of being sensitive, linear and provide a satisfying isolation in comparison to other types of uncouplers.

The electronic circuit may comprise a power supply which preferably comprises a battery operated power source.

The second power supply preferably has a floating ground.

The uncoupler(s) preferably have a floating ground.

Preferably, the uncoupler(s) used in the circuit for generating the stimulating electrical field and the uncoupler(s) used in the circuit of the detector have a floating ground. Such configurations allow reducing the interference between the detector and the stimulating electrical field.

The detector preferably comprises two electrodes which are respectively connected to the inverting and non-inverting inputs of a differential amplifier, each electrode preferably being connected to a respective input of the differential amplifier and to a constant current source through a corresponding resistor.

The electronic circuit is preferably symmetrical.

Processing of the Measured Signal

The processing can be carried out by any computer, such as a personal computer, a microprocessor, a smartphone, or any integrated signal processing device capable of performing calculus. Any analog-digital card may be used in addition to the computer.

The invention is also characterized in other of its aspects by the originality of the phenomenon used to detect or analyze the species. Said phenomenon is a random fluctuation of concentration, of a type that was considered in prior art as a spurious artifact and a nuisance, and which is put to useful work in the invention. The useful measure of this fluctuation also requires some specific analysis methods. Notably, thus, in some of its aspects the invention relates to a method in which a signal is recorded, and only a random and non-periodic fluctuating part of said signal is used as a reporter of a concentration of a species.

This method also requires some specific signal processing methods. Thus in another of its embodiments, the invention relates to a digital or analogic data processor, programmed in such a way as to extract from a signal random and non-periodic components, and to extract from said components a value reflecting the averaged or integrated amplitude of said components. Preferably, said amplitude depends on the concentration of some selected species in said medium.

Optional Pre-Treatment

The signal obtained from the detector electrodes or the optical detector, e.g. integrative light detector, is preferably recorded as a function of time.

In some embodiments, said signal may be pre-treated, e.g. by noise reduction, filtering, demodulation or integration methods, and more generally by signal processing methods, numerical or analogic, known by those in the art.

The signal obtained from the detector electrodes or the optical detector may be filtered.

The signal obtained from the detector electrodes or the optical detector may be modulated in amplitude, said signal preferably having the same frequency as the polarization signal.

Preferably, when the detection electrodes are polarized by the polarization signal as described above, the filtering may reduce, preferably eliminate, frequencies different from a frequency of the polarization signal, e.g. frequencies of the stimulating electrical field.

The signal obtained from the detector electrodes or the optical detector may be stored in a storage unit, e.g. in a computer via an acquisition card, said acquisition card may control the detector and the stimulating electrical field generator. The acquisition card may be controlled by the computer via software e.g. Labview Signal Express, or Matlab, or other mathematical or experimental software, or other more generic software like C, C++, Java, and the large variety of programmation software well known from those of the art.

The signal obtained from the detector electrodes or the optical detector may be frequency-demodulated, preferably at a frequency of less than 1 kHz, preferably less than 100 Hz and possibly at low as 10 Hz, and sometimes between 100 and 1 Hz.

The use of such frequencies for demodulation advantageously allows reliably retracing in a DC signal the passage of the aggregate in the detection zone.

The fluctuations or variations of the variable are preferably obtained after such a demodulation.

Analysis of the Fluctuations or Variations of the Variable

The device preferably comprises a digital processor to perform a time-dependent or a space dependent analysis, preferably wavelet analysis, or an autocorrelation on the variations of the electrical variable or on the image issued from an imaging detector, or on the output of an integrative optical detector.

Preferably, step b) comprises processing by a time-dependent or space dependent analysis, preferably by wavelet analysis, or by autocorrelation analysis of the variations measured at step a).

It is possible to use a digital or analogic processor enabling extraction from the fluctuations or variations of the conductivity signal, or of the integrated optical signal, information about the strength of random and/or non-periodic features, and preferably enabling extracting from said information a quantitative value reflecting the strength of said features. Particularly preferably, the amplitude of the components provides information on the concentration of the charged species in the liquid medium.

In some preferred embodiments, said quantitative information is the integral over time of an autocorrelation function, for instance a mean square deviation.

In some other preferred embodiments, said quantitative information is the spatial integral over an image of the space, of an autocorrelation function, for instance a mean square deviation.

In some yet preferred embodiments, said quantitative information is a coefficient corresponding to a given wavelet of the wavelets basis, or a set of such coefficients, or a function of such coefficients, said coefficient being obtained by applying to the said signal a wavelet analysis In some other preferred embodiments, said quantitative information is a coefficient corresponding to a given wavelet of the wavelets basis, or a set of such coefficients, or a function of such coefficients, said coefficient being obtained by applying a spatial wavelet analysis to an image.

The use of such processors advantageously allows distinguishing fluctuations or variations of the measured variable e.g. from spurious electronic noise or baseline drift.

The fluctuations or variations may be processed by an analysis aimed at extracting their temporal fluctuations.

Optionally, the results of such an analysis performed on fluctuations or variations measured while a stimulating electrical field is applied are compared to the results of such an analysis performed on fluctuations or variations measured when the stimulating electrical field is not applied and/or to a reference value obtained in the absence of the species to detect.

Temporal Analysis

In particularly preferred embodiments, the temporal fluctuations or variations of the variable are processed by wavelet analysis.

In short, wavelet analysis comprises convoluting a function, here temporal fluctuations or variations of a variable, with a set of functions called wavelets (a wavelet basis), having a common shape but different characteristic timescales.

The wavelets have the property of being of null average, and in contrast with e.g. Fourier transform, decrease to zero at a distance from a single point or "center".

Beside these common properties, wavelets can take a variety of shapes, and thus be tuned to extract, from a complex and noisy signal, features with some specific characteristics of shape or duration.

Wavelet analysis is particularly well adapted to the processing of fluctuations of the variable obtained when carrying out the invention.

Various shapes of wavelets may be used in the invention, depending on the characteristics of the stimulating electrical field and of the space. Some exemplary and not limitative ones are exemplified in example 5.

The method of the invention may involve decomposing the signal onto a wavelet basis, selecting a subset of the wavelet basis in which the difference of wavelet amplitude between a blank negative signal and a positive sample is maximal, and extracting the final signal from said subset.

In a preferred embodiment, the amplitude of wavelets from this subset, when applied to a blank or negative control, is essentially null, and the amplitude of said wavelets on a positive signal (for instance with optically detectable aggregates) is non-zero.

In one embodiment, the analysis comprises performing an autocorrelation analysis. As an exemplary and non-limitative example, said autocorrelation analysis involves calculating the integral over all or part of the signal, of $<(I(t)-<I(t)>)^2>/<40^2>$ where $I(t)$ is the intensity of light at time t, and brackets represent an average over time.

This corresponds to a mean square analysis, but other different modes of integration may be used, provided said integration extracts from data a quantitative value, or a series of quantitative values, e.g. related to the development of macroions aggregate.

Spatial Analysis

Spatial fluctuations of the variable may be measured and used for extracting a signal, e.g. using an imaging device which takes instantaneous images encompassing a plurality of aggregates and performing a spatial image analysis.

In an embodiment, said imaging device may be a CCD or a CMOS camera.

An image of an area of the space, submitted to the stimulating electrical field may be taken and optionally recorded, as exemplified in FIG. 8 or 11B An analysis aiming at extracting fluctuations of light intensity and/or of light color in said area may then be applied.

Optionally, the results of such an analysis performed on fluctuations or variations measured while a stimulating electrical field is applied are compared to the results of such an analysis performed on fluctuations or variations measured when the stimulating electrical field is not applied and/or to a reference value obtained in the absence of the species to detect.

In one embodiment, the analysis comprises performing an autocorrelation analysis. As an exemplary and non-limitative example, said autocorrelation analysis involves calculating the integral over all or part of the image, of $<(I(r)-<I(r)>)^2>/<I(t)^2>$ where $I(r)$ is the intensity of light at point r, and brackets represent an average over the image, or over a selected area A of the image.

This corresponds to a mean square analysis, but other different modes of integration may be used, provided said integration extracts from data a quantitative value, or a series of quantitative values, e.g. related with the development of macroions aggregate.

In particularly preferred embodiments, the spatial fluctuations or variations of the variable are processed by wavelet analysis.

In this embodiment, one operates as above for time dependent fluctuations or variations, except that one uses as the starting function a space-dependent light intensity map, and convolutes it with a set of two dimensional functions or wavelets (a wavelet basis), having a common shape but different characteristic scales.

Wavelet analysis is particularly well adapted to the processing of fluctuations of the variable obtained when carrying out the invention.

Various shapes of wavelets may be used in the invention, depending on the characteristics of the stimulating electrical field and of the space.

Preferably, the area A in which the analysis is performed is chosen to encompass only parts of the total image viewed by the camera, in which the medium comprising the macroions is present.

Preferably, too, in order to have a good averaging effect, the area A is selected in order to contain at any given instant a multiplicity of aggregates.

BRIEF DESCRIPTION OF THE DRAWINGS

The invention will be better understood from a reading of the detailed description below, of non-limiting examples for its implementation, and from examination of the attached drawings, in which:

FIG. 2 shows an example of detection electronics used in a device according to the present invention, FIG. 2A shows the circuit corresponding to the preamplifiers used in detection electronics implemented in the present invention.

FIG. 10A shows the principle of branched rolling circle amplification (RCA), FIG. 10B shows padlock probes and ligation templates for branched rolling circle amplification, FIG. 10C shows the creation of large and branched DNA products, FIGS. 11A and 11B show the results of an electrophoresis separation, FIG. 12 shows the applied voltages as a function of the electrokinetic mode, FIG. 13 shows electrokinetic separation of RuBipy at different concentrations A 1 mM B 50 µM, different detection methods being used: fluorescent (red) and conductimetric (black), FIGS. 16A and 16B show fluorescence microscopy images of aggregates obtained after carrying out a HRCA amplification method for different incubation times, respectively 15 minutes and 30 minutes, FIG. 17 show the evolution of parameter QDna after a wavelet analysis for different amplification durations.

EXAMPLES

Principle of Detection

Contact conductivity measurement in µchip-CE or electrokinetic-based methods offers a relatively simple method to detect conductivity changes in a liquid by using integrated electrodes in direct contact with the background electrolyte in the microchannel.

The Electric field was decoupled from HVPS and conductivity detectors by using different external potential references. This was achieved here thanks to floating-reference, isolation amplifiers, as will be specified below.

Figure 1A:
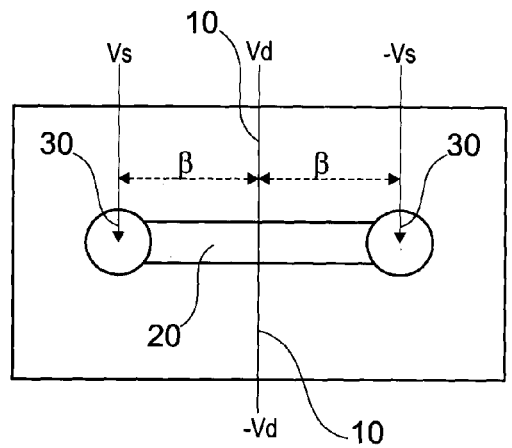
FIG. 1c) shows a schematic diagram of a device according to the invention.
FIG. 1b) shows three pairs of electrodes for conductivity measurement in contact mode (ECMC) with associated detection zones, FIG. 1a) shows the configuration of voltages used for creating the electrical field and detecting the charged species.

Detector electrodes 10 were positioned and configured relatively to applied voltages, according to FIG. 1a, and connected to the detection electronic device 50. Electrodes 10 may be Pt planar microelectrodes, as detailed below.

This figure shows that balanced voltages (Vs, −Vs) are supplied from a high voltage power supply 40 (HVPS) to both side of microchannel 20 and balanced conductivity detection voltages (Vd, −Vd) are applied on the transverse channel electrodes 10 by the detection device.

The detector electrodes 10 are positioned in a configuration perpendicular to the main excitation field, and at a point along the microchannel 20 corresponding to a null electric potential in the reference system of excitation electrodes 30.

The potential drop across the detection electrodes 10 is also minimized by keeping these electrodes narrow independently from the channel dimensions.

Example 1: Structure and Fabrication Process for a Microfluidic System to be Used in the Invention in a Conductivity Detection Mode The microchip is a Glass/PDMS (Polydimethylsiloxane) hybrid microfluidic chip fabricated by rapid prototyping following D. C. Duffy et al, Analytical chemistry, 1998, 704974-84.

It consists of two layers: a PDMS layer and a glass substrate which supports electrodes for conductivity measurement in contact (ECMC) fabricated by lift-off.

The PDMS layer, on top, contains a microchannel with two reservoirs (2.5 mm of diameter) at its 2 extremities for solution injection. Electrodes for conductivity measurement in contact mode (ECMC) consist of two planar and miniaturized Pt electrodes with 50 μm width, 25 μm gap and 200 nm thickness, facing each other perpendicularly to the microchannel.

Figures 1B, 1C:
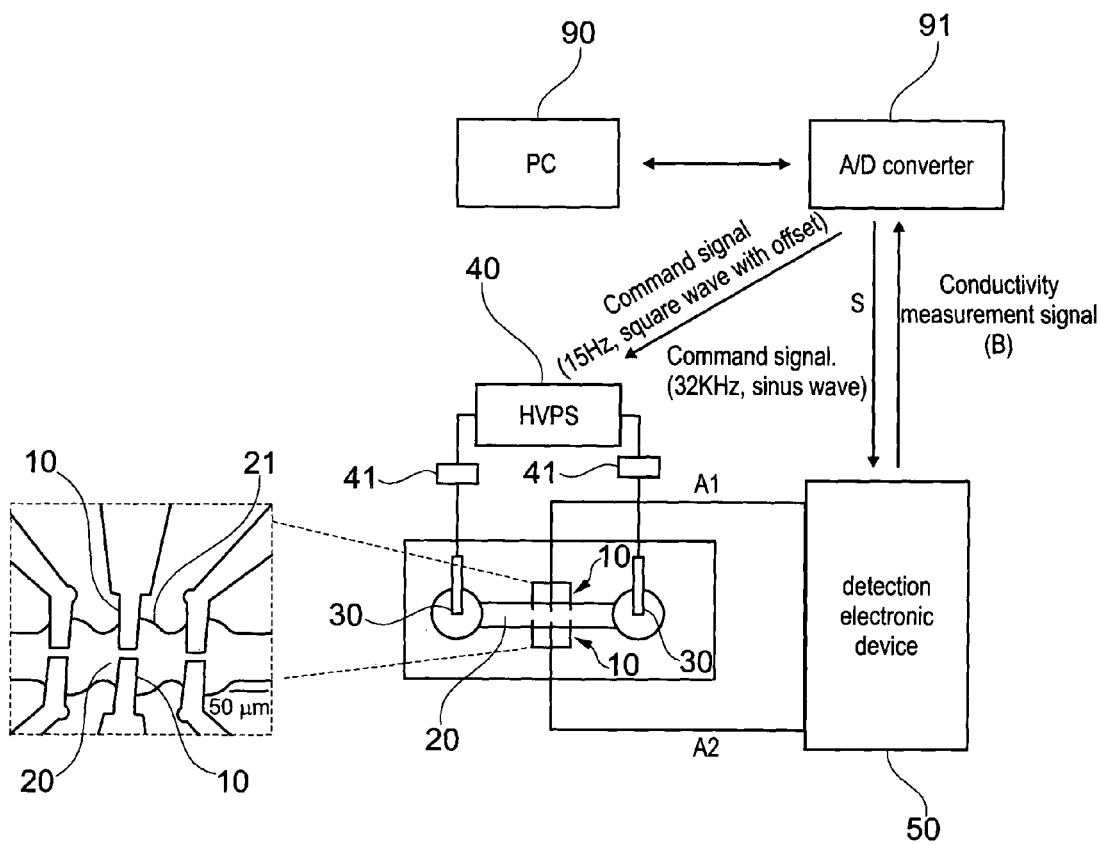

FIG. 1b) shows three pairs of electrodes 10 for conductivity measurement in contact mode (ECMC) with associated detection zones. Only one is used for measurements.

Electrodes are prepared by lift-off of a 200 nm Pt layer (a 20 nm Cr layer is used as adhesion layer) deposited by sputtering (Emitech, K575) on a 2 μm 1813 photoresist layer. The PDMS and glass layers are aligned and irreversibly bonded using a 30 s oxygen plasma treatment (Harrick plasma).

The microchannel is 5 mm length, 40 μm high and 150 μm wide except in the detection zone in the middle of microchannel, where the width is 160 μm.

As mentioned above, locally enlarging the channel at the detection zone facilitates decoupling between the ECMC and the high voltage power supply (HVPS) by decreasing locally the driving field intensity, without significantly affecting aggregates formation, which occurs all along the channel. In addition, this enlargement 21 also facilitates the alignment of ECMC in the detection zone.

Example 2: Detection Electronics to be Used in the Invention

As mentioned above, achieving an efficient decoupling between the HVPS and the detection electronic device is not an easy task, due to residual leakage current flows through the protective ground conductor present in all mains-powered electronic equipment.

Minute electrical leakage currents through the ECMC may create electrolysis, resulting in the formation of gas bubbles inside the microchannel.

A system with floating ground based for example on 6 lithium batteries (ultralife, 9V) was used as shown in FIG. 2. This system was used as a power supply by three isolation amplifiers such as ISO124P, two voltage controlled current sources 55, one bridge of resistors 56 and one differential amplifier 57 to get an all-electronic, portable and simple device, with a high sensitivity.

The measurement bandwidth of the device is limited by that of the isolation amplifiers.

This system is connected to a pair of electrodes 10 embedded in a microchip, according to the general synthetic scheme provided in FIG. 1c.

The used detection device combines two isolation techniques, the first one is electrical, with the amplifiers of isolation 53, 54 and measurement, the second one is geometrical, with the symmetry, to overcome the very high sensitivity of the microfluidic systems of capillary electrophoresis to electromagnetic interferences during detection of conductivity in contact.

The device ensures an excellent electrical decoupling with the electrophoresis high voltage and an excellent detection sensitivity.

Hereunder are detailed each part of this system. Each of the isolation amplifier 53, 54 have a gain of 1 and all the system uses a dual power supply (±).

Isolation Amplifier

Isolation and measurement amplifiers 53, 54 were chosen because of their immunity to common mode interference, their low cost, their excellent linearity, their limited size and their high measurement sensitivity.

For example, ISO124 isolation amplifier is used, which has a common mode rejection ratio of 160 dB in low frequency and a bandwidth of 50 kHz.

The presence of isolation amplifiers 53, 54 eliminates a ground loop due to leakage currents.

Pre-Amplifiers

Pre-amplifiers 80 at the detection device input are made with operational amplifiers (OPA) OPA2132 (Burr Brown).

Pre-amplifiers allow accurate adjustment of adjusting signal amplitude because the processing chain functions in symmetrical mode.

Resistors preferably have a tolerance of ±1%. The circuit is given at FIG. 2A, the following equations being satisfied:

$$S_1 = -S\frac{R_2}{R_1} \text{ and } S_2 = -S_1\frac{R_5}{R_4}$$

Low Pass Filters

The ISO124 delivers noise signals of about 500 kHz frequency.

In order to obtain solely the useful signal, a second order low-pass filter with a bandwidth of approximately 50 kHz was placed at the output of each of the isolation amplifier.

Figure 2B:
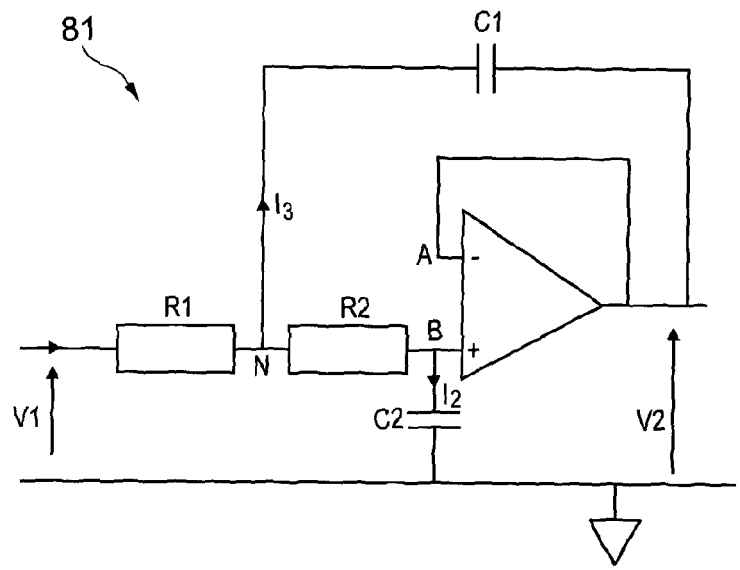
FIG. 2B shows the circuit corresponding to the low-pass filters used in the circuit of FIG. 2.

The circuit corresponding to this low pass filter 81 is shown in FIG. 2B.

In linear regime, assuming the OPA is ideal and noting p=jω, the low-pass filter has the following transfer function:

$$H = \frac{V_2}{V_1} = \frac{1}{1 + (R_2 + R_1)C_2 p + R_1 R_2 C_2 C_1 p^2}$$

This transfer function H is a transfer function of a second order low pass filter with the following cutoff pulsation:

$$\omega_0 = \frac{1}{\sqrt{R_2 R_1 C_1 C_2}}$$

In the device used, the cutoff frequency $$f_0 = \frac{\omega_0}{2\pi}$$

was about 50 kHz.

The low-pass filters suppress ripple voltages from isolation amplifiers.

Offset Control

In order to minimize the offset voltages of the amplifiers of the processing chain, a global offset control 82 was used.

Figure 2C:
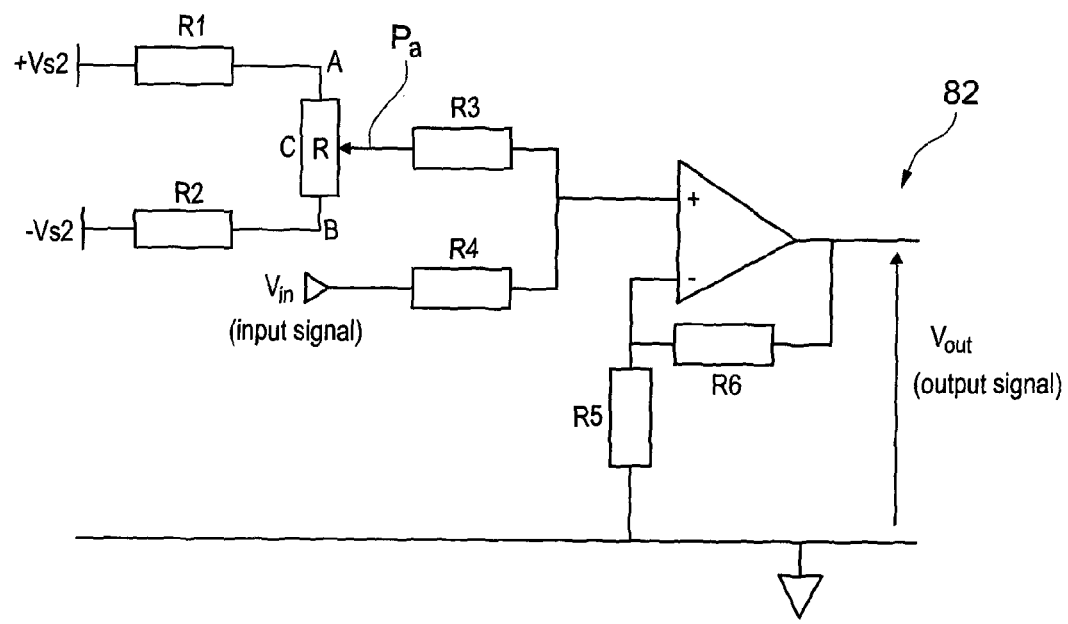
FIG. 2C shows a circuit used to minimize the offset voltages of the amplifiers.

The circuit uses a summing non inverter OPA having a gain equal to 1 (FIG. 2C).

$$V_{out} = (V_{in} + V_{offset}) \frac{R_6}{R_5}$$

The offset signal $V_{offset}$ is set by the divider bridge $R_1$, $R_2$ and Pa (potentiometer cursor). If the potentiometer cursor is at A, $$V_{offset} = \frac{V_{s2}}{3};$$

and if it is at B, $$V_{offset} = \frac{-V_{s2}}{3};$$

and if it is at C, $V_{offset}=0$. The signal $V_{out}$ is the sum of the offset signal with the input signal $V_{in}$.

In the circuit used, $V_{s2}$ and $-V_{s2}$ are ±9V batteries. Thus, it is possible to control between +3V and −3V the global offset of the processing chain upstream the offset control thus constituting a high control dynamic.

Voltage Controlled Current Sources (VCCS)

The impedance of the load (i.e. solution between the detectors) is about several dozens of MOhm for most buffers in CE (e.g. between 30 MOhm and 50 MOhm for TE1×), and the output impedance of the isolation amplifier is about several MOhm in low frequency and decreases at high frequency.

A source may properly conduct current into a load if the output impedance of the source is at least 10 times greater than the impedance of the load.

Isolation amplifiers such as the ISO124 may not deliver current in a load of more than 500 kOhm from a few KHz.

Thus, voltage controlled current sources 55 (VCCS) were used. Current sources indeed have a quasi infinite output impedance and can thus deliver current in very high impedance loads.

Figure 2D:
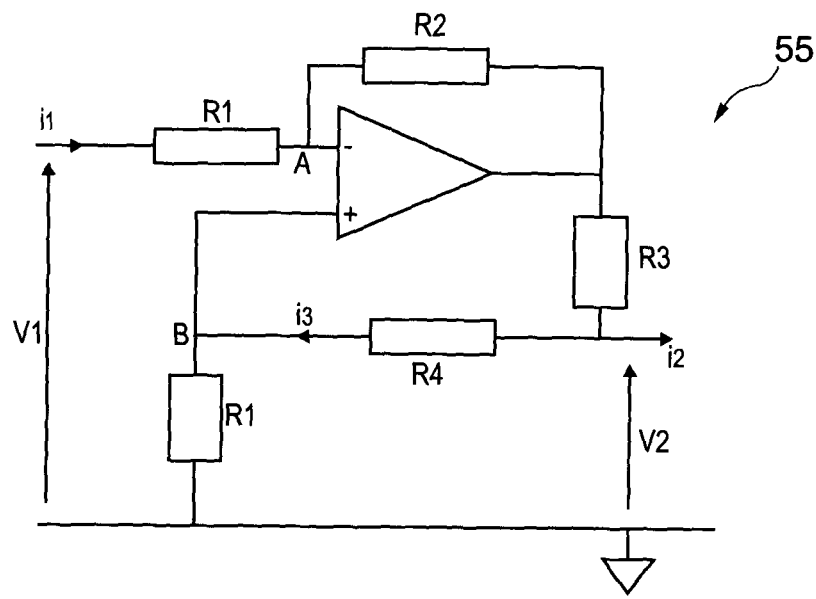
FIG. 2D shows an amplifier circuit.

The circuit used is shown in FIG. 2D and satisfies, in a linear regime, the following relation:

$$i_2(t) = -\frac{R_2}{R_3 \times R_1} V_1(t)$$

If voltage $V_1(t)$ is set in shape, amplitude and frequency, then the current $i_2(t)$ is set in shape, amplitude and frequency.

Thus, the features of the current delivered by the controlled current sources only depend from the control voltage. Thus, in the circuit used, the currents delivered by the two sources are symmetrical as control voltages of the isolation amplifier.

Bridge of Resistors and Conductivity Measurement

The measurement of the conductivity of the solution between the detectors is performed through a resistor bridge having as input the output of a controlled double current source.

The resistor bridge acts as a current divider. The two VCCS act as a bipolar current generator.

Figure 2E:
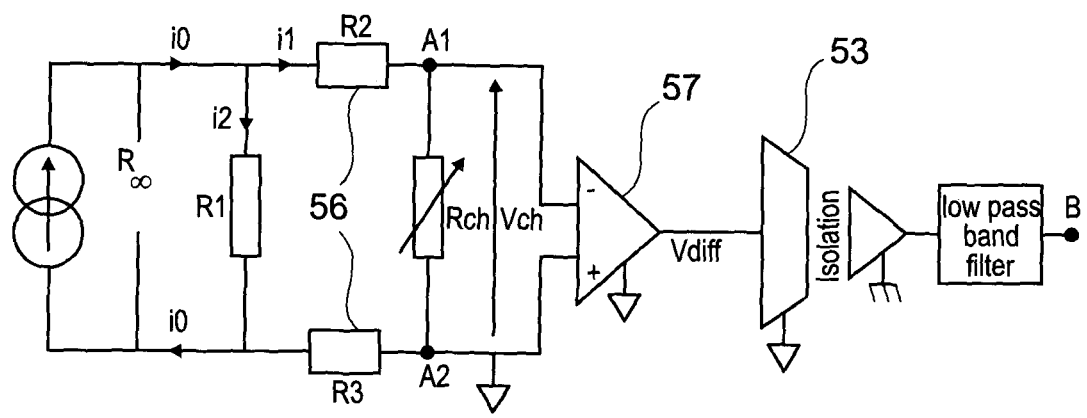
FIG. 2E shows a circuit corresponding to a voltage controlled current source.

The equivalent circuit of FIG. 2 is the following (the circuit upstream of the resistor bridge is modeled by a bipolar current generator) (FIG. 2E).

$$i_0 = i_1 + i_2$$

with $$i_1 = i_0 \times \frac{G_2 + G_{ch} + G_3}{G_2 + G_{ch} + G_3 + G_1} \text{ and}$$

$$i_2 = i_0 \times \frac{G_1}{G_2 + G_{ch} + G_3 + G_1}$$

$$\left(G_x = \frac{1}{R_x} \text{ being conductance of } R_x\right)$$

The voltage $V_{ch}$ at the load $R_{Ch}$ (solution between the detectors) terminals satisfies:

$$V_{ch} = R_{ch} \times i_1$$

The voltage $V_{diff}$ at the output of the differential amplifier is:

$$V_{diff} = V_{ch} \times \text{Gain}$$

Features (shape, intensity and frequency) of $i_0$ are set by the source and do not vary during the measurement.

Thus, any variation of the voltage at the load terminals (solution between the detectors) is linked to the variation of the resistance of the load (variation of the conductance of the solution between the detectors).

One can note that the variation of the impedance of the load also leads to the variation of currents $i_1$ and $i_2$ such as $i_0=i_1+i_2=$constant.

The variation of voltage $\Delta V_{ch}$ at the load terminals satisfies the following equation:

$$\Delta V_{ch} = \Delta R_{ch} \times i_1 + \Delta i_1 \times R_{ch}$$

The integrated differential amplifier allows suppression of the noises and to amplify the useful signal without interfering with current $i_1$.

The input of the isolation amplifier is the differential output voltage of the differential amplifier. The isolation amplifier ensures transmission (in isolation mode) of the signal to the data acquisition peripheral for analysis. The filter suppresses the noise inherent to the functioning of the isolation amplifier.

Example 3: High Voltage Power Supply (HVPS)

Figure 3:
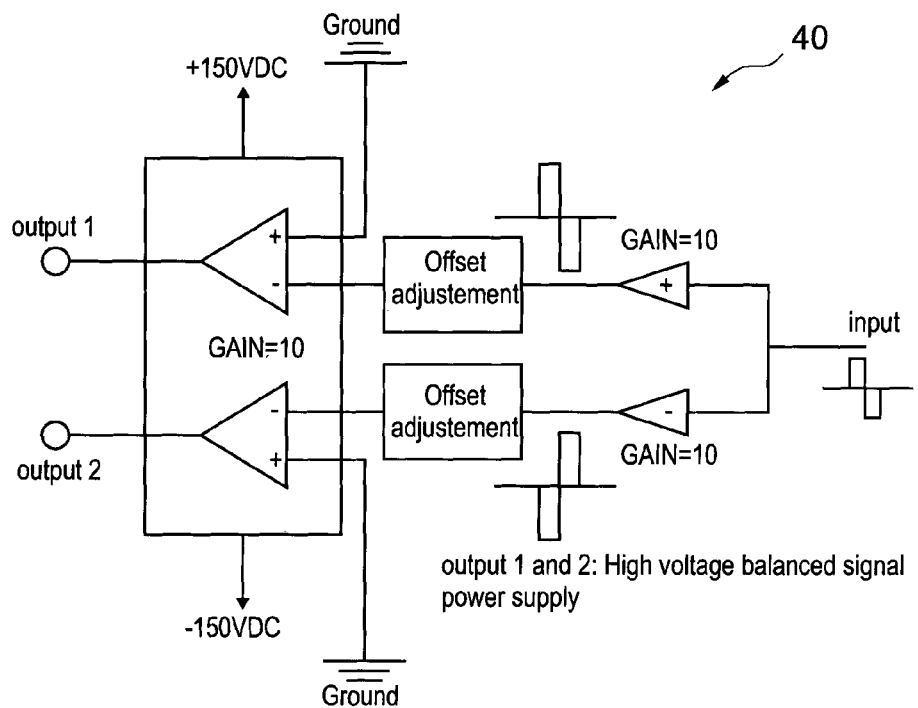
FIG. 3 shows a diagram of the balanced circuit designed for the high-voltage power supply (HVPS)

This power supply is also a balanced circuit. It consists for example of 2 high voltage amplifiers contained in the low-cost dual high voltage amplifier PA242/APEX (Farnell, France), powered by a converter EMCO FS05CT-15 (Condatas AG, CH). The centre-lead of the converter is connected to the ground (FIG. 3), ensuring stability of the system with regards to external fields and user security.

A 50 Ohm resistor attenuator 41 is preferably used between the ECMC and the electronic detection device in order to prevent interference due to the impedance mismatch between the alimentation line (50 Ohm) via HVPS and the detection electronic device.

This system is connected to stimulating electrodes 30, located in the entrance and exit wells of the microchannel as described in example 1. The stimulating electrodes may be made out of a Pt wire.

Example 4: Preparation of DNA Samples for Detection of DNA Amplification by Long-Range PCR DNA Sequences—

The PCR primers were designed by Perl Primer for the target region of DNA lambda based on positions 22179 to 32161. The forward primer is 5'-GACCATCGGGG-TAAAACCGTCTATGAC-3' (SEQ ID NO: 1), and the reverse primer is 5'ATGACGACTTATTGCCGCTCTGT-TCCC-3' (SEQ ID NO: 2) (Sigma Aldrich, France).

PCR Protocol—

DNA lambda was obtained from lambda cl857 Sam? (Roche, France) and reconstituted in DNase/RNase free Water (Gibco, France) at various concentrations. The PCR mix (50 µl) consists in lx long range PCR Buffer (QIAGEN, France), 400 nmol of forward and reverse primers, various quantities of lambda DNA, 2 units of long range PCR Enzyme Mix (QIAGEN, France).

The thermal cycling involves an initial denaturation at 93° C. for 3 min followed by 2 amplification sequences. The first 10 cycles were carried out with the following thermal sequence: 93° C. for 15 s (denaturation), 62° C. for 30 s (annealing) and 68° C. for 10 min (extension). The following cycles were set as: 93° C. for 15 s (denaturation), 62° C. for 30 s (annealing), 68° C. for 10 min+(n−10)×20 s (extension), where n is the cycle number. Thermal cycling was carried out in a Biometra T-Professional thermocycler.

For some validations (see correlation measurements, in Results section), it was useful to separate the produced DNA from the PCR mix. For that we first suspended the raw PCR mixture after thermocycling in 500 µl of TE (1×) buffer, then separated the 10 Kpb DNA from this suspension by using a 100K membrane (centrifugal filter, Millipore, France) at 12.000 g for 12 min.

Of course, the sequences, DNA sources, amplification kits, thermocycler and cycles protocols are only illustrative and not limitative.

The method is fully generic and can be applied to many different samples and kits. Also, in the example described here, the amplification is performed out of the chip, and the products are then loaded into the detection chips. 10 µl of DNA solution from 10 kpb PCR reaction are introduced in one of the reservoirs of the microchip and flown through the microchannel by pressure. The associated instrumentation, comprising driving electrodes in the reservoirs and connection to the detection microelectrodes, is then connected to the microchip according to FIG. 1C.

In some other preferred embodiments, the amplification is performed directly on chip, by placing such chip in a thermal control module.

Example 5: Example of Analysis of Conductivity Data According to the Invention Using a Conductivity Fluctuation Detection Mode First the possibility to use the method according to the invention to expand cycle-number dependent Q-PCR strategies to long-range PCR was tested.

In order to validate the method according to the invention, the PCR was performed out of the chip, the products were checked by conventional gel electrophoresis and the raw product of the reaction was injected into the microfluidic chip.

FIG. 1C shows a schematic of the set-up. 10 µL of DNA solution from 10 kpb PCR reaction is introduced into one of the reservoirs of the microchip and flown through the microchannel by pressure.

The associated instrumentation, comprising driving electrodes in the reservoirs and connection to the detection microelectrodes, is then connected to the microchip according to FIG. 1C.

To create and monitor DNA aggregates, the DNA solution was subjected to a low frequency, high voltage alternating current (AC) signal (square wave, 320V/cm maximum amplitude, 15 Hz frequency) with a small direct current (DC-OFFSET) signal (40V/cm). The AC signal is used to create DNA aggregates with maximum efficiency without depleting too fast the microchannel from its DNA content, and the DC-offset facilitates monitoring, by driving the aggregates across the detection electrodes at a constant velocity, and constantly renewing the solution in the electrodes region.

For conductivity measurements, on the ECMC was applied a polarization signal consisting of a balanced AC signal at 32 kHz (sine wave) with maximum amplitude ranging from 1 to 2V at the measurement output B of the electronic detection device.

At this frequency and in contact mode, the impedance is essentially conductive. All electronic devices were controlled by a computer 90 via an analog-digital converter card 91 such as NI-USB 6380X and the NI-signal express software (National Instruments, France).

The sampling frequency was set at 320 ksamples/s and the data from conductivity measurement were stored on computer before frequency demodulation. The frequency demodulation processed each set of 32000 samples by Fourier transform to give an effective collection rate of 10 Hz, using the tone extraction functionality of NI-signal express software. In the following this 10 Hz demodulated signal is referred to as the conductivity signal.

As known in the art, see eg. H. Isambert, et al, Physical Review Letters, 1997, 78, 971-974. DNA aggregates in solution have a higher ion density than the bulk, causing a change of amplitude of the conductivity signal when these aggregates cross the detection zone. This detection principle has the advantage of being label-free.

Figure 4:
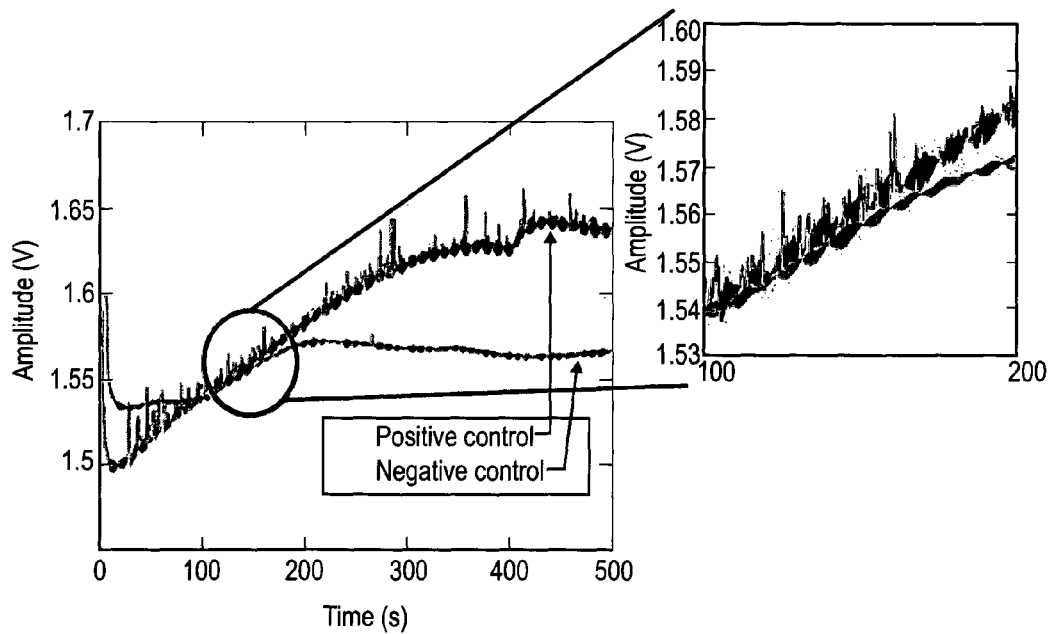
FIG. 4 shows a conductivity measurement signal obtained after carrying out a method according to the invention.

FIG. 4 shows examples of conductivity signals based on 10 Hz frequency demodulation of 32 kHz conductivity measurement signal obtained from raw PCR solutions of negative (without DNA) and positive (with DNA target) control as prepared in example 4 after 38 cycles of amplification.

For both positive sample and negative control, a monotonous baseline drift was observed, and a high frequency noise with an irregular roughly periodic pattern. Because of these artefacts, the robust extraction of the signal requires specific signal processing tools.

An analysis based on wavelet transform was used (see Results and Discussion section below).

Procedure of Wavelet Analysis

In the present detection scheme, the 10 Hz conductivity signal S (t) is sampled at time points $t \in \{0, \tau_0, 2\tau_0, \ldots, T=N\tau_0\}=\Omega$, and the flow of DNA aggregates appears as a random series of transient jumps (FIG. 4).

Figure 5:
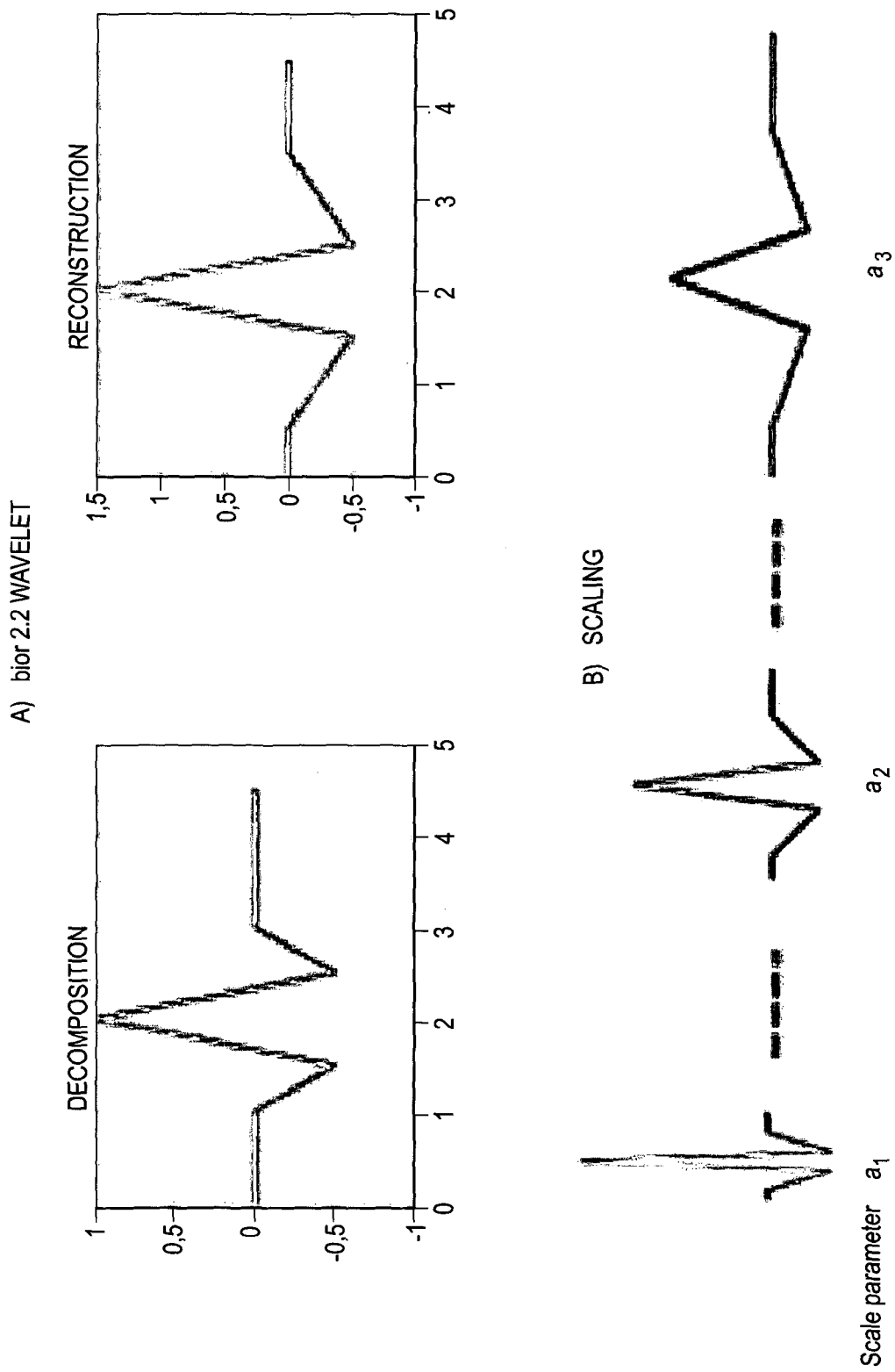
FIG. 5: A) shows the bior2.2 wavelet from biorthogonal wavelet family. In order to achieve exact reconstruction (no loss of information), this wavelet family uses two wavelets, one for the decomposition and one for the reconstruction of the signal. B) Schematic rescaling.

These jumps are superimposed onto a high frequency noise, a low frequency baseline drift, and large amplitude transients. In order to separate these different components and retain only the physically significant ones, wavelet analysis was used. The input signal is convoluted with a set of functions (a wavelet basis) generated from an appropriate local functional pattern, that best matches the transient events of interest. By trial and error, the biorthogonal wavelet called "bior2.2" was chosen. This wavelet is defined by the elementary real decomposition function ψ(t) and reconstruction function φ(t) (FIG. 5A). The basis is generated as the 2D set of functions {ψ$_{a,\delta}$(t)} by time-translation and rescaling ψ(t) as follows (FIG. 5B):

$$\psi_{a,\delta}(t) = \frac{1}{\sqrt{a\tau_0}} \psi\left(\frac{t-\delta}{a\tau_0}\right)$$

With $a \in \{2^j\}_{j \in \mathbb{N}}$ and $\delta \in \Omega$. $a\tau_0$ is the scale, but it is further referred to as a dimensionless scale a.

In this basis, S(t) is represented by a set of coefficients $d_s(j,k)$ obtained by discrete wavelet transformation, i.e. by the convolution:

$$d_s(j,k) = \int_0^T S(u) \psi_{2^j, k\tau_0}(u) du$$

Figure 6:
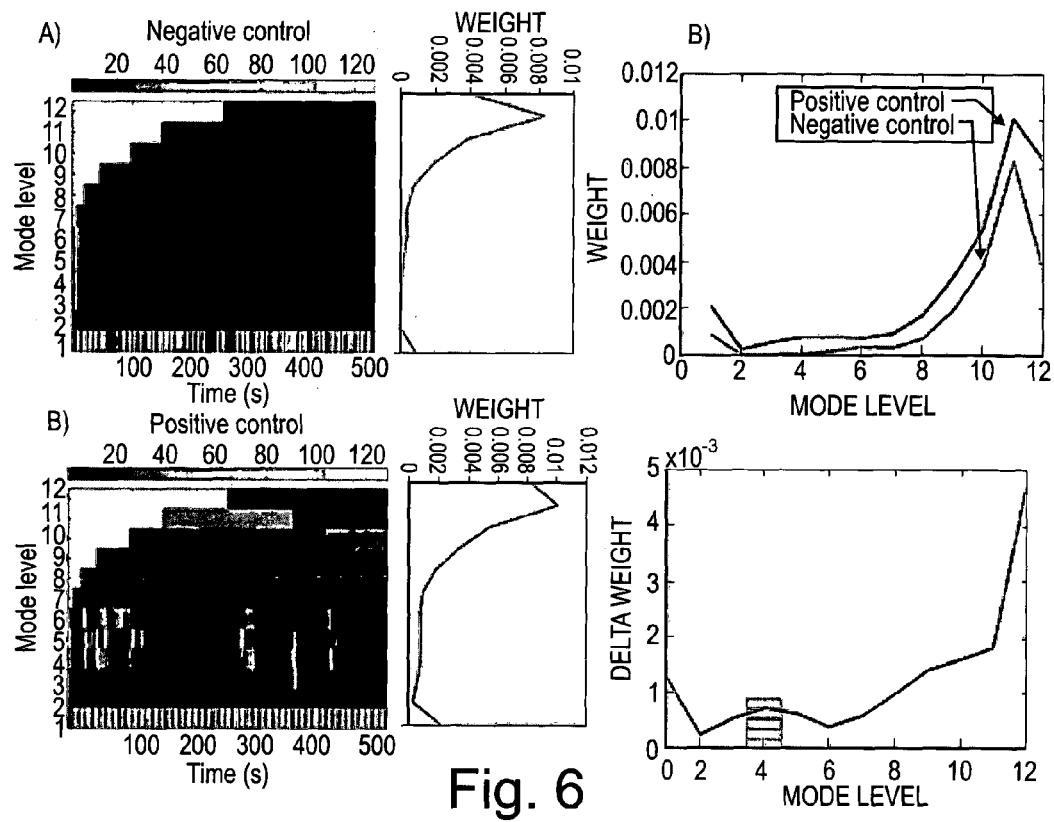
FIG. 6: A) shows Discrete Wavelet Transform spectrum ($d_s$ (j, k) coefficients) of the positive and negative control signals of FIG. 4 for $0 \leq j \leq 11$ using the bior2.2 decomposition wavelet. B) shows corresponding weights and weight difference (delta weight) of detected DNA aggregates.

For a typical signal, the decomposition is represented as a color-coded spectrum as shown in FIG. 6A, showing the coefficients $d_s(j,k)$ in terms of mode level (j) as a function of time (k). From this representation, and by analogy with the power spectrum computed in Fourier analysis, the weight for each model level $2^{j_0}$ is computed as:

$$W(j_0) = \frac{1}{T} \sum_{k=1}^{T} |d_s(j_0, k)|$$

Weight functions were computed from spectra obtained with and without DNA (FIG. 6A), and then compared (FIG. 6B). DNA transients consistently contributed the largest signal-to-noise ratio at the time-scale $2^3\tau_0$ corresponding to the 4th mode level ($j_0$=3). The signal was therefore reconstructed at this scale by:

$$S_{j_0}(t) = \sum_k d_s(j_0, k) \phi_{2^j, k\tau_0}(t)$$

where $\phi_{2^j, k\tau_0}(t)$ is translated and rescaled from φ.

Figure 7:
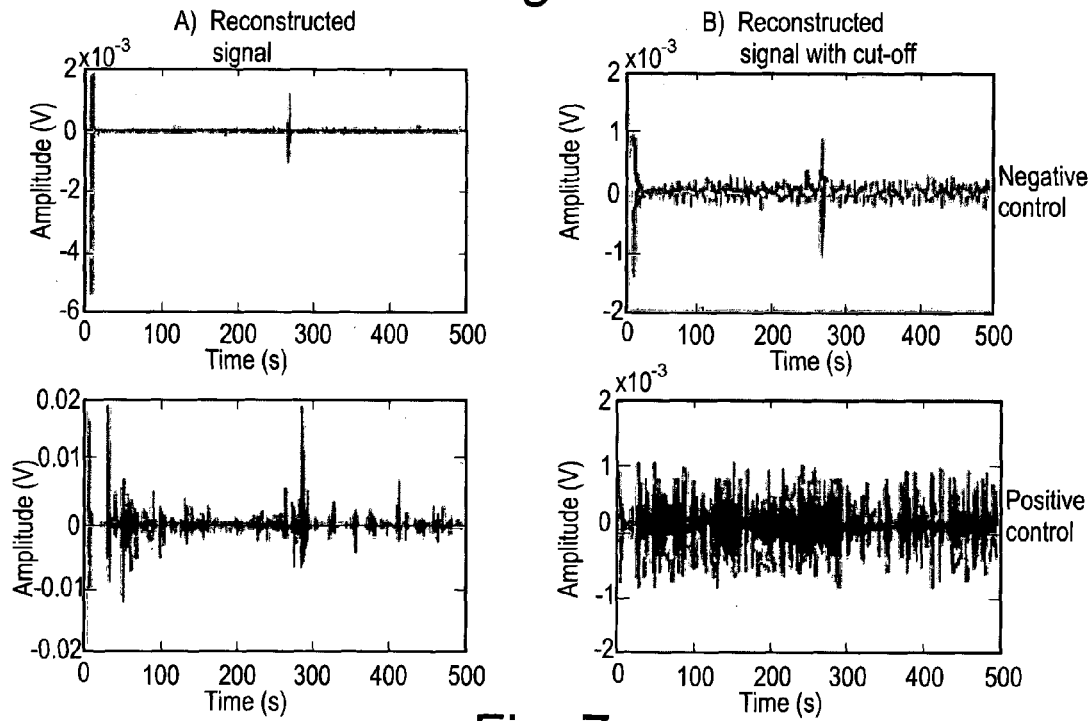
FIG. 7 shows the reconstructed signals (positive and negative control) based on scale-time $2^3 \tau_0$ ($4^{th}$ mode level) without (A) and with (B) cut-off for amplitudes larger than 0.002.

The reconstructed signal $S_3$ (t) is expected to reflect the presence of DNA aggregates (FIG. 7A).

$S_3$ (t) was chopped with a cut-off at 0.002 which left $S_3$ (t) unchanged at most time points. This threshold exceeds the time-average of $|S_3(t)|$, at maximal DNA concentrations (after 41 amplification cycles), and most of the relevant conductivity fluctuations remain below the cut-off (FIG. 7B).

The amount of DNA QDna was finally assessed in relative terms by the time-average of $\widehat{S_3(t)}$, the signal reconstructed from the 4$^{th}$ mode ($j_0$=3) and cut-off at 0.002. The same cut-off is applied to all samples.

$$Q\text{Dna} = \langle \widehat{S_3(t)} \rangle$$

Example 6: Implementation of the Invention with an Optical Imaging Detection Mode and Comparison Between Imaging and Electric Detection Modes Microscopy Aggregates of macroions are monitored using imaging fluorescence microscopy. In order to have an independent monitoring of DNA aggregates for validating the method, in some experiments the chip prepared in example 1 was placed on top of an inverted microscope Aviovert 135TV (Zeiss) in epifluorescence mode, with a 10× objective (Nikon). DNA is prepared as in example 4, and is subsequently fluorescently labelled by Sybergold, allowing a simultaneous detection by fluorescence and conductivity. For fluorescent dye concentrations under 1×, no significant influence of the labelling on conductivity detection was observed.

Correlation Observations

The ability of the invention to selectively detect DNA aggregates was tested by simultaneously recording the conductivity signal, fluorescent images and local fluorescence signal in the gap between the electrodes.

Figure 8:
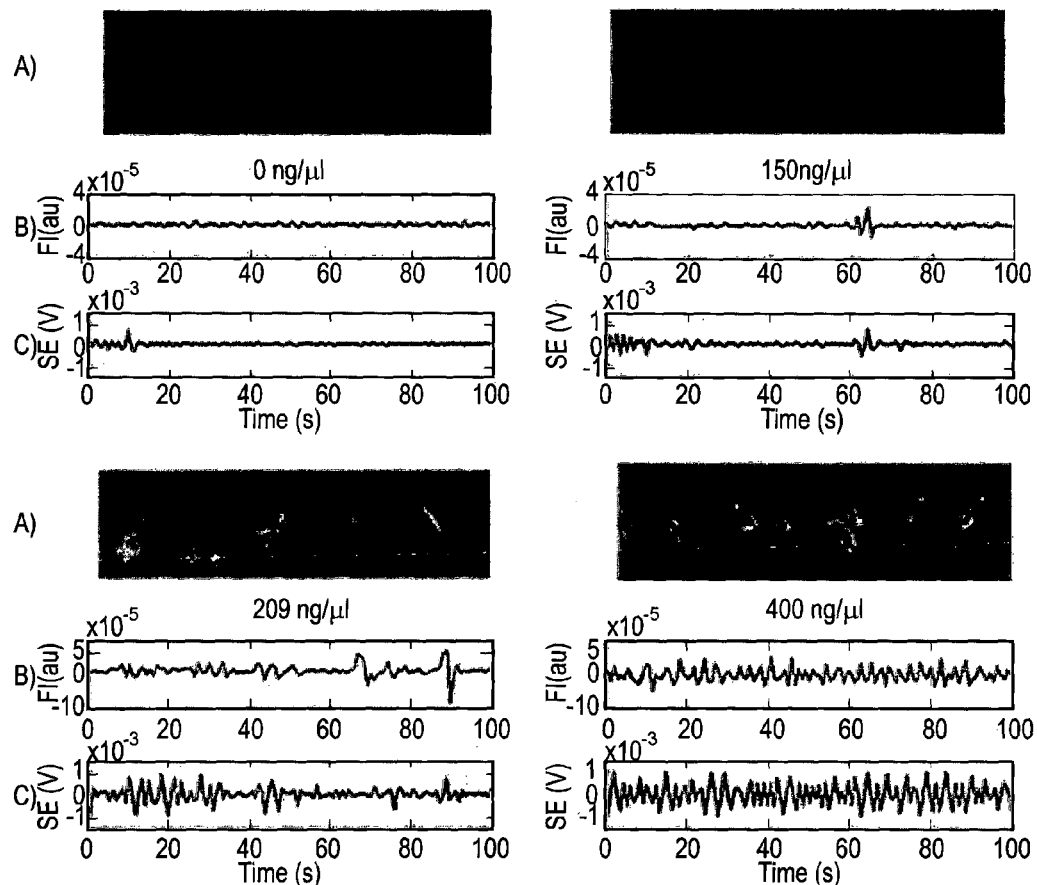
FIG. 8: for increasing amounts of 10 kbp DNA, extracted from the PCR mixture, suspended in TE (1×) buffer and labeled with Syber Gold, comparisons are shown between: A) fluorescence imaging, B) the time-derivative of the ratio of the fluorescence intensity measured in the detection zone to its time-average value C) the conductivity signal (SE) based on DNA aggregates extracted by the wavelet analysis procedure (SE). (reconstructed from the $4^{th}$ mode level (j=3) with cut-off at 0.002)

These experiments were performed for different concentrations of 10 kpb DNA from PCR reactions, previously extracted from the PCR mixture (see Example 4), suspended in TE (1×) buffer and labelled with SybrGold (FIG. 8). Each measurement was performed during 130 s and the first 30 seconds of the signal were discarded in order to let the system reach its steady state (typically, aggregates reach their maximal size and intensity within a few seconds from an initially homogeneous solution). The 10 Hz conductivity signal was processed according to the time-dependent wavelet analysis procedure described in example 5.

The fluorescent signal was processed as the time-derivative of the ratio of the fluorescence intensity measured in the detection zone to that outside the microchannel (background). The concentration threshold for creating DNA aggregates in this buffer was 200 ng/μl. A good correlation was observed between the visual appearance of aggregates, the processed fluorescence signal and the processed conductivity signals.

Two dimensional wavelet analysis of the images given in FIG. 8 can also be processed using the same wavelet analysis procedure as described in example 5, except for the wavelet basis which is now a set of two dimensional wavelets.

Example 7: Use of the Invention to Implement Label-Free Quantitative Long Range PCR In PCR, the concentration of DNA after n cycles depends on the amount of target DNA and on the number of cycles n. It is expected to increase linearly with the initial DNA amount for a fixed value n. As a function of n, this amount is expected to increase exponentially in a first phase (call the exponential phase), and then saturate to a finite value, independently of the initial DNA concentration.

In quantitative PCR (qPCR), the inflexion point of the plot of DNA concentration versus number of cycles (or, for some other treatment algorithms, the point at which the intensity reaches a predefined threshold) is considered as a reliable way to quantify the initial DNA concentration.

The sensitivity of the detection method was assessed by applying it to the quantification of long-range PCR amplification products. 10 kbp DNA solutions from long-range PCR reactions, prepared according to the protocol described in example 4, were loaded without separation from the PCR mixture and without labelling. Various mixtures were prepared, with different initial amounts of DNA lambda (from 0 to 2.5 ng) and different numbers of amplification cycles (from 0 to 41 cycles). The total duration of each measurement was 530 s.

Figure 9:
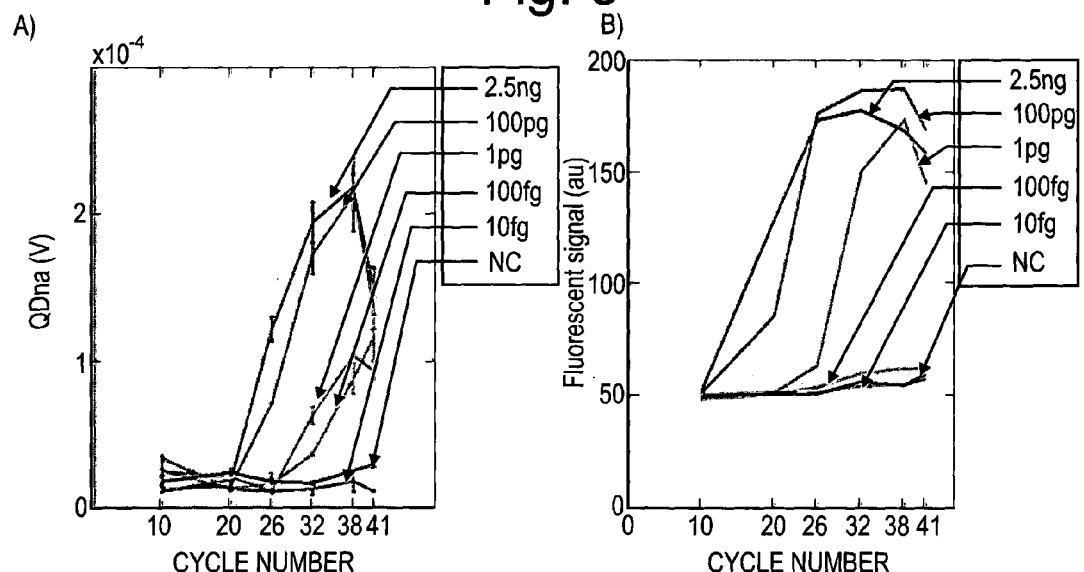
FIGS. 9A-9B show in A) Label-free quantification of DNA using the wavelet analysis procedure (QDna) for various amount of target DNA (10 fg, 100 fg, 1 pg, 100 pg, 2.5 ng) at various amplification cycles (10, 20, 26, 32, 38, 41). The standard deviation for each point in the panel was calculated from 3 measurements from 3 different aliquots. B) shows corresponding densitometric analysis of gels performed as control on samples used for label-free detection. C) shows complete images of the gels and densitometric considered area.

DNA amplification was quantified by wavelet analysis (FIG. 9A). For all samples initially containing more than 10 fg/µl of DNA, the amount of DNA QDna (see example 5) significantly increases with cycle numbers, showing that the limit of detection (LOD) of the present method lies between 10 and 100 fg/µl of initial DNA.

This detection sensitivity is better by about one order of magnitude than that obtained by fluorescence detection following gel electrophoresis performed as a control on the same samples (FIG. 9B).

Additionally, the total volume of solution in the chip is only 1 µl from the initial 50 µl of PCR product. So with full integration of the PCR in the chip, this technology should easily yield a sensitivity of a few fg of initial DNA, since this corresponds to the product of less than 100 lambda DNA copies.

The inflexion points of the curves also shift towards smaller numbers of cycles, showing that the invention can be used to perform quantitative long-range PCR, an achievement not possible with the fluorescent methods of prior art, in which quantitative PCR is performed only with small fragments, typically smaller than 1000 kbp.

Example 8: Use of the Invention in Conjunction with Isothermal Amplification of DNA by Branched RCA The invention is particularly advantageous in conjunction with isothermal nucleic acids amplification methods, because first said methods are easy to implement in microchannels or microchambers, not requiring thermal cycling, and second because several of these methods naturally lead to large DNA products, even when starting from short templates, thus extending the range of application of the invention.

Here we demonstrate this with branched rolling circle amplification (RCA), as described e.g. in Nilsson et al., Nucleic Acids Research, vol. 30, no. 14 e66, pp. 1-7, 2002.

The principle of the method is known in the art, and can be summarized by FIG. 10A. A target DNA (ligation template) is put in the presence of a linear "Padlock probe", the end of which are respectively complementary to two sides of the ligation template. In a first step, the two DNA hybridize, creating a section of fully paired duplex DNA, and the padlock probe is circularized by a ligase. Example of padlock probes and ligation templates used here are shown in FIG. 10B.

Padlock probe (200 nM) was ligated in 10 mM tris-acetate buffer pH7.5, 10 mM magnesium acetate 50 mM, 1 mM ATP, 1 µg/µl BSA and 0.2 U/µl T4 DNA ligase (Ameresham Pharmacia Uppsala, Sweden), at 37° C. for 30 mn, in the presence of 600 nM ligation template.

The circularized DNA was then amplified using Phi29 polymerase with universal primers (random priming). This amplification was performed using the kit Illustra Templiphi (GE Healthcare life sciences), and the protocol distributed with this kit.

The kit comprises a sample buffer, a reaction buffer, and an enzyme mix. The sample buffer contains the random primers, the reaction buffer contains the salts and buffers and the deoxynucleotides.

Briefly, 0.5 µl of the input DNA sample is added to 5 µl of sample buffer, and the mix is heated at 95° C. for 3 mn (activation phase). After cooling, this mix is mixed again with 5 µl of reaction buffer, and incubated at 30° C. for 4 hours (amplification phase)

The principle of operation of this kit is exemplified in FIG. 10C, showing how it creates large and branched DNA products.

As a control, an aliquot of a product is loaded on an electrophoresis gel and separated (FIG. 11A), the control is on the left (performed without template), the size reference 1 kb ladder (middle), and positive reaction product (right). In the right lane, the band remains in the loading well, confirming that mostly large DNA (much larger than the DNA in the ladder) is successfully created in the reaction.

Then, another aliquot of the amplification product is loaded into a microchannel prepared according to example 1, submitted to a stimulating field similar to that used in example 4. The fluctuations of concentration induced by the field are recorded as a function of time, in the imaging mode described in example 6. The recorded images (FIG. 11b), show the appearance in a time of 15 to 30 s, of a heterogeneous light intensity in the observation area, demonstrating the presence of aggregates, and the successful operation of the invention following isothermal amplification. The 4th panel in FIG. 11b shows that when DNA is depleted from the channel, a uniform and dark background is recovered.

In another embodiment, the reaction may be performed isothermally directly in the microchannel containing the electrodes, to detect the amplification by a direct conductivity reading, following the same protocol as in example 5.

Example 9: Application to Inorganic Ions Detection

Chip Structure

The microchip is a Glass/PDMS (Polydimethylsiloxane) hybrid and consists of two layers. The PDMS layer, on top, contains a microchannel with two reservoirs (2.5 mm of diameter) at its 2 extremities for solution injection. Electrodes for conductivity measurement in contact mode consist of two planar Pt electrodes with 50 µm width, 25 µm gap and 200 nm thickness, facing each other perpendicularly to the microchannel. Electrodes are prepared by lift-off of a 200 nm Pt layer (a 20 nm Cr layer is used as adhesion layer) deposited by sputtering (Emitech, K575) on a 2 µm 1813 photoresist layer. The PDMS and glass layers are aligned and irreversibly bonded using a 30 s oxygen plasma treatment (Harrick plasma). The microchannel is 40 µm high and 150 µm wide except in the detection zone where the width is 160 µm. Others microchip dimensions are reported in FIG. 12. The effective length both for fluorescent and conductimetric detection is of 2 cm.

Detection Electronics

The system described in relation to FIG. 1C was used with floating ground based on 6 lithium batteries (ultralife, 9V), a power supply by 3 low-cost isolation amplifiers ISO124P, 2 voltage controlled current sources, 1 bridge of resistors and 1 differential amplifier to get an all-electronic, portable and simple device, with a high sensitivity. The measurement bandwidth of the device is limited by that of the isolation amplifiers, i.e. 50 kHz.

High Voltage Power Supply

The same power supply as in example 3 was used.

Different electrokinetic modes were carried out, the voltages applied using this HVPS are reported in FIG. 12.

Background Electrolyte (BGE)

The background electrolyte consists in a MES (2-(N-morpholino) ethanesulfonic acid)/His (Histidine) buffer at 20 mM pH 6.

Sample: Tris(2.2'-Ru(bipy)$_3$$^{2+}$ridyl) dichlororuthenium(II) (see structure below) was first used as model compound as it can be detected by conductivity measurement as well as by fluorescence (FITC filter)

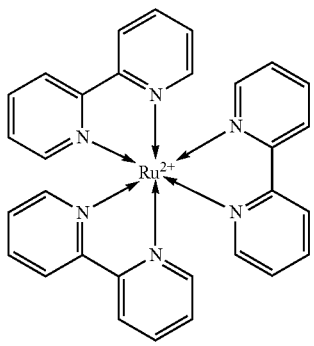

Tris(2.2'-Ru(bipy)$_3$$^{2+}$ridyl) dichlororuthenium(II) Structure

RuBiPy was first used as model cation as it can be detected by conductimetric and fluorescence detection.

The voltages applied for both loading and separation are reported in FIG. 12. These experiments were carried out in MES/His buffer as it is a low conductive buffer due to its quasi-isoelectric properties.

In order to compare the sensitivity achieved with fluorescence and conductimetric detection, different concentrations of Rubipy were injected ranging from 50 µM (FIG. 13B) to 1 mM (FIG. 13A).

These results showed at low sample concentration that despite the low electrophoretic mobility of this model cation, the signal to noise ratio is 10 times higher using conductimetric detection than with the fluorescent one.

Figure 14:
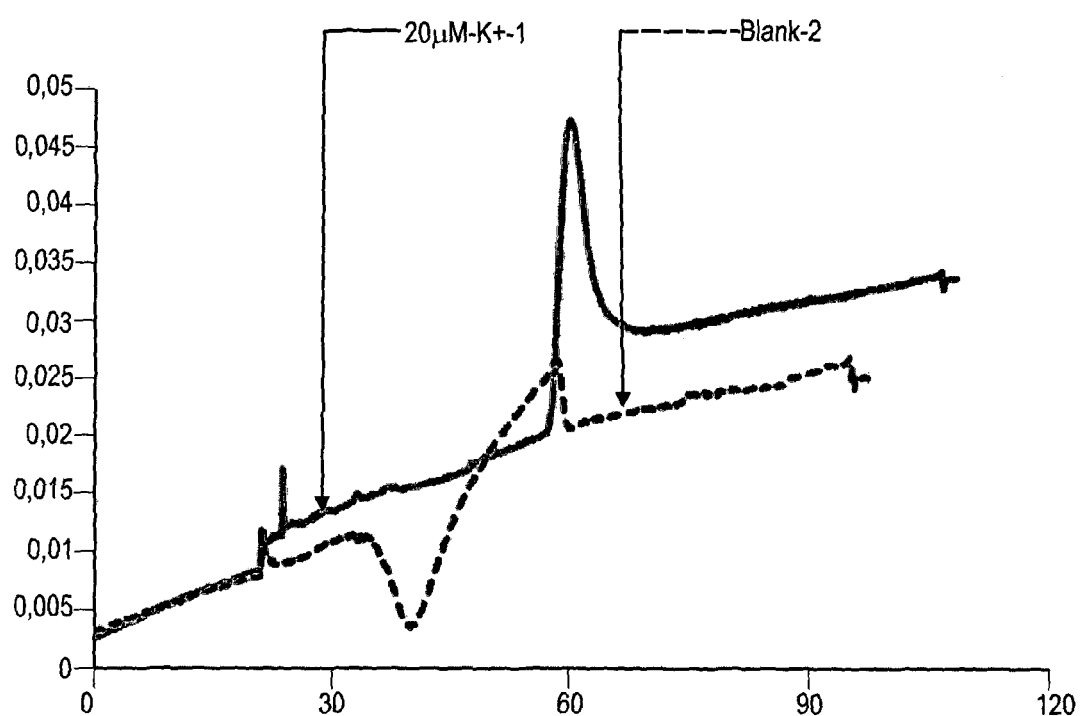
FIG. 14 shows electrokinetic separation of K$^+$ at 20 µM compared with an injection of buffer.

Thereafter an inorganic cation of interest, K+, was first injected individually at 20 µM (FIG. 14) and compared with a blank consisting in replacing the sample by the buffer.

Even at this low concentration, the signal to noise ratio is quite high with the method according to the invention, one can thus expect a low sensitivity for such inorganic cations.

Example 10: Conductimetry Signal Processing by a Wavelet Analysis

Figure 15A:
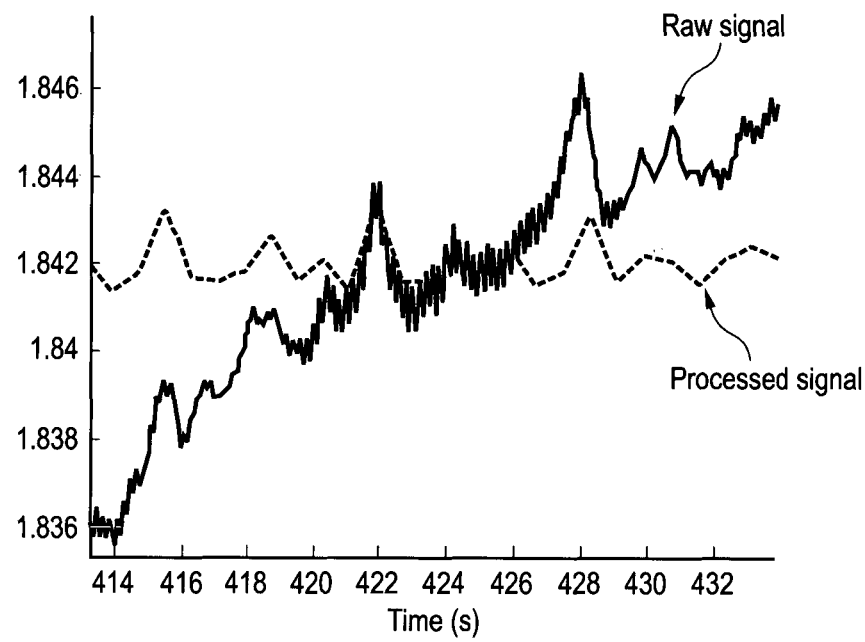
FIG. 15A shows a comparison of a raw signal obtained from the detection module and of the corresponding signal obtained after processing by a wavelet analysis.

FIG. 15A shows a comparison of a raw signal obtained from the detection module and of the corresponding signal obtained after processing by a wavelet analysis. The signal was processed by a level 4 wavelet (temporal support of 0.8 s).

An offset of 1.842V was added to the processed signal for it to be displayed at the same level as the raw signal. The raw signal was obtained after a detection of aggregates obtained from a lambda-DNA solution (5 kbp) at 69 µg/ml.

Figure 15B:
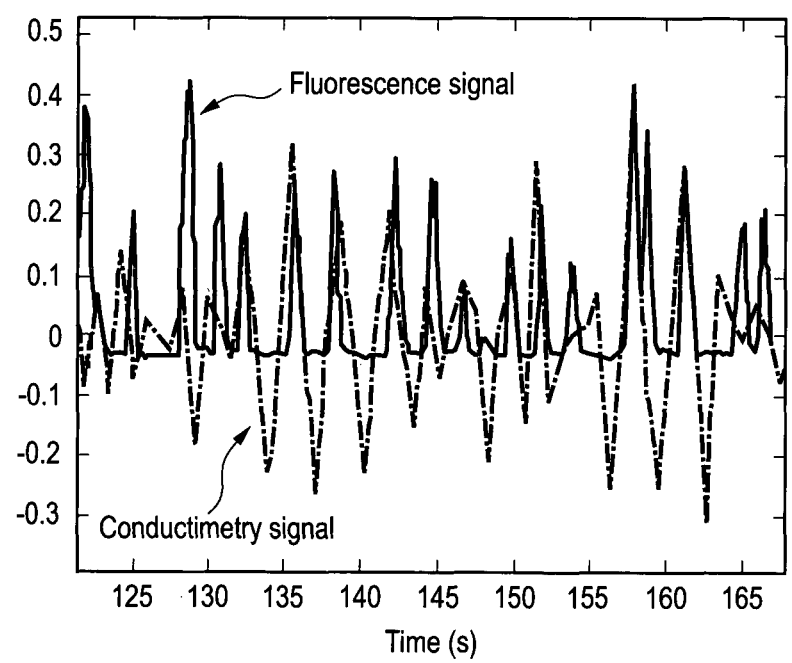
FIG. 15B shows a correlation between a fluorescence signal and a conductimetry signal.

The electrical parameters were:
Stimulating voltage: 440V/cm
Frequency of the stimulating voltage: 15 Hz
Medium conductivity: about 50 mS/m Example 11: Correlation Between Fluorescence Signal and Conductimetry Signal FIG. 15B shows a correlation between a fluorescence signal and a conductimetry signal processed by a level 4 wavelet. The units are arbitrary.

The signals were obtained from the detection of aggregates obtained from a branched RCA solution at 30 minutes of incubation. The DNA was made fluorescent by adding SyBr Green at a concentration 0.25×.

The electrical parameters were:
Stimulating voltage: 440V/cm
Frequency of the stimulating voltage: 10 Hz
Medium conductivity: 500 mS/m more or less 100 mS/m.

The buffer used for FIG. 15B is the second buffer solution of example 12 detailed below.

Example 12: Buffer Solutions

Buffer solutions having the hereunder detailed compositions can be used in a HRCA amplification method in view of carrying out the method according to the invention.

The first buffer solution comprises for 20 µL:
LongRange PCR Enzyme Mix 10× (QIAGEN): 1.75 µL, and
Pure water: 18.25 µL, The first buffer solution further comprises the following components at the hereunder detailed concentrations:
Bovin serum albumin (BSA): 0.1 mg/mL,
Tris HCl: 6 mM,
MgCl2: 1.25 mM,
(NH4)2SO4: 1.25 mM, and
Dithiothreitol (DTT): 0.5 mM The second buffer solution comprises for 20 µL:
LongRange PCR Enzyme Mix 10× (QIAGEN): 2 µL, and
Pure water: 18.25 µL.

The second buffer solution further comprises Bovin serum albumin (BSA) at a concentration of 0.1 mg/mL.

The first buffer solution has a conductivity of 630 mS/m more or less 100 mS/m and corresponds to a preferred embodiment. The second buffer solution has a conductivity of 400 mS/m more or less 100 mS/m.

Example 13: Use of the Invention in Conjunction with Amplification of DNA by HRCA In this example is reported the test of detection of HRCA products obtained ex situ, outside the detection micro fluidic chip.

The protocol used for the off-chip HRCA is hereunder detailed.
HRCA Protocol

The circularisation protocol of Nilsson (M. Nilsson, M. Gullberg, F. Dahl, K. Szuhai, and A. K. Raap. Real-time monitoring of rolling-circle amplification using a modified molecular beacon design, *Nucleic Acids Research*, vol. 30, no. 14 e66, pp. 1-7, 2002) was carried out.

As a positive control, we took the target and probe having the hereunder described sequences (provided by Eurogentec, Belgium). As a negative control, the target was replaced by the buffer of the circularisation reaction.

Probe (ppWT):
P-CTGCCATCTTAACAAACCCTTTCCTCTATGATTACTGACCTACGACC

TCAATGCTGCTGCTGTACTACTCTTCTATGCGATTACCGGGCT

-continued

Target (tWT):
GTTTGTTAAGATGGCAGAGCCCGGTAATCG

The probe (200 nM) was ligaturated in 10 mM Tris-acetate pH 7.5, 10 mM magnesium acetate, 50 mM NaCl, 1 mM ATP, 1 μg/μl BSA and 0.2 μl T4 DNA ligase (Amersham Pharmacia Biotech, Uppsala, Sweden) at 37° C. during 30 minutes with 600 nM of ligation template.

The amplification uses Phi29 polymerase with random primers (random hexamers) and takes as input the circular DNA obtained at the preceding step. This amplification is carried out using the amplification kit Illustra Templiphi (GE-Healthcare Life sciences) and allows the obtaining of branched double-stranded DNAs. The amplification kit comprises: a sample buffer, a reaction buffer and an enzyme mix. The reaction buffer comprises the salts, the deoxynucleotides, is adjusted to a pH convenient for DNA synthesis, and contains the random primers at a final concentration of 0.02 mg/mL.

Very briefly, a volume of 0.5 μl of input DNA was added to 5 μl of sample buffer and the resulting volume was heated to 95° C. during 3 minutes to obtain a denaturation of the double-stranded DNAs. This volume once cooled down was mixed with 5 μl of reaction buffer and the mixture was incubated at 30° C. during different durations (varying from 10 minutes to 2 hours). The reaction was done in a thermocycler and the enzyme was unactivated at 65° C. at the end of the reaction.

In a first experiment, a saline buffer having a conductivity of 1.75/m was used in the liquid medium containing the DNA to be aggregated. This led to an electrolysis phenomenon around the stimulating electrodes which reduced the accuracy of the detection method according to the invention.

However, the use of a buffer solution according to the invention, consisting of a Long-Range PCR buffer (Qiagen) and of BSA at 0.1 mg/ml (corresponding to the second buffer solution of example 12 above) led to a decrease of the conductivity of the solution to 0.255/m without affecting the amplification efficiency. This buffer allowed the creation of instabilities without creating an electrolysis phenomenon around the stimulating electrodes (FIGS. 16A and 16B).

Small aggregates are visible from 15 minutes of amplification. They reach an optimal size around 30 minutes.

It is possible to detect the presence of aggregates of HRCA products obtained after amplification durations greater than 30 minutes, using the wavelet modes 3 et 4 (FIG. 17). The detection was carried out while the aggregates of the HRCA products were present in their amplification buffer. The error bars correspond to the standard deviations of the measures made.

The parameter Q corresponds to the time-average of the reconstructed signal obtained after the wavelet analysis and this parameter can be used to make a quantitative measurement of DNA concentration in the device.

The measurement is quantitative with a clear increase of the measured signal after 20 minutes of incubation.

Example 14: Use of a Plurality of Detection Zones

Figure 18:
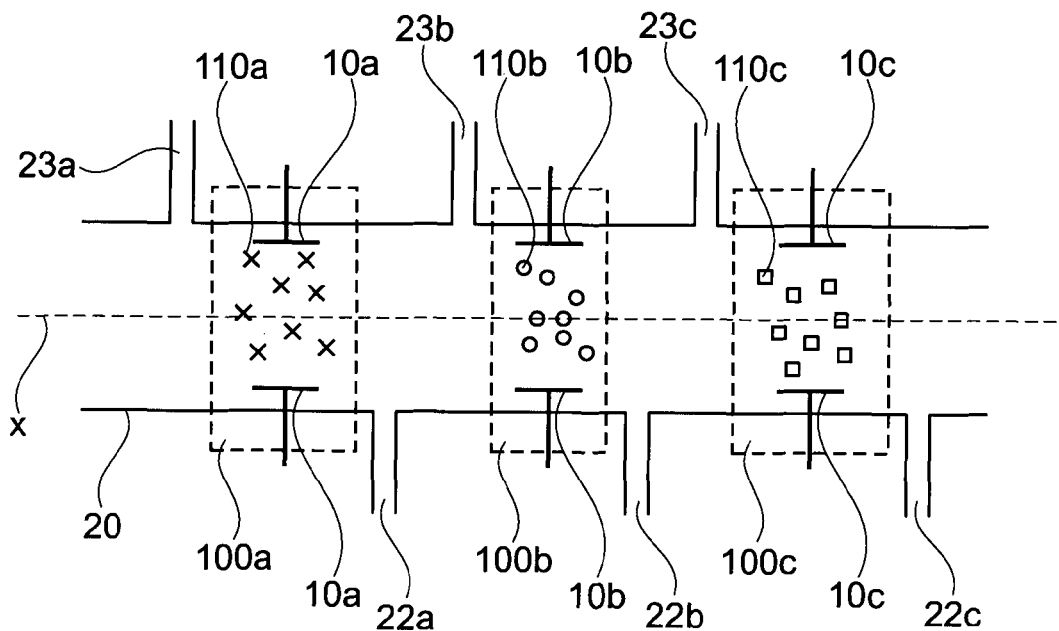
FIGS. 18 and 19 show other embodiments of methods according to the invention wherein detection is carried out in a plurality of detection zones.

FIG. 18 shows an embodiment of the invention wherein the micro-channel 20 is elongated along a longitudinal axis X, a plurality of detection zones 100a, 100b and 100c succeeding along the longitudinal axis X.

A couple of electrodes 10a, 10b and 10c is present in each of the detection zones 100a, 100b and 100c for measuring fluctuations within the liquid medium of an electrical variable depending on the concentration of the nucleic acids in the liquid medium.

Each of the detection zones 100a, 100b and 100c comprises different compounds 110a, 110b and 110c, said compounds e.g. being primers able to interact with different sequences of nucleotides of the nucleic acids to be detected.

The compounds 110a, 110b and 110c can be connected, e.g. fastened, to the walls of the micro-channel 20 and/or to the walls of the input channels 22a, 22b and 22c and/or to the walls of the output channels 23a, 23b and 23c.

An alternative electric field can be applied to make the macro-ions stay in a detection zone during a duration appropriate for detection.

Figure 19:
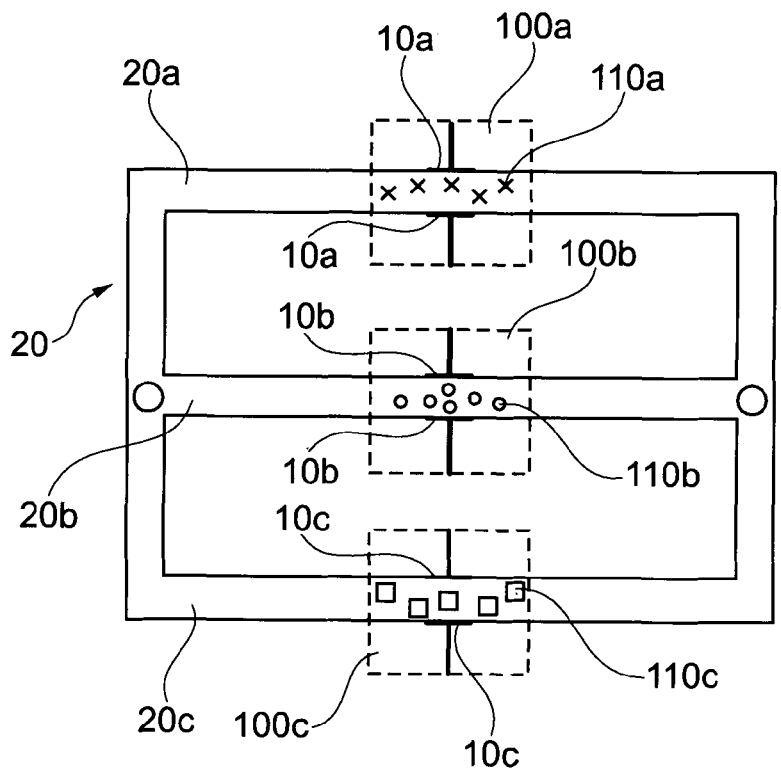

FIG. 19 shows a variant wherein the detection zones 100a, 100b and 100c are present in different sub-channels 20a, 20b and 20c which are not in fluidic communication.

The expression "comprising a/one" should be understood as "comprising at least one".

The expression "comprised between . . . and . . . " should be understood with the end points included.

The expression "comprising" should be understood as "comprising at least".

The invention claimed is:

1. A method of detecting macroions in a liquid medium contained in a space, comprising:
   a) submitting the liquid medium to a stimulating electrical field to induce formation of aggregates of macroions, the aggregate formation creating random spatial fluctuations of the macroion concentration in the liquid medium,
   b) measuring, in a detection zone of the space, spatial and/or temporal fluctuations within the liquid medium of at least one variable depending on the concentration of said macroions in the liquid medium, and
   c) determining, based on these fluctuations, the presence of the macroions.

2. The method according to claim 1, the formed aggregates of macroions not comprising any additional labeling agent.

3. The method according to claim 1, step c) comprising processing by a time-dependent or space dependent analysis, by wavelet analysis, or by autocorrelation the fluctuations measured at step b).

4. A method according to claim 1, wherein the macroions are polyelectrolytes and aggregates of polyelectrolytes are formed at step a).

5. The method of claim 4, the polyelectrolytes comprising nucleic acid, or nucleic acid strands having 5 kilobases or more or 5 kilobase pairs or more, or 10 kilobases or more or 10 kilobase pairs or more, or nucleic acid aggregates being formed at step a).

6. The method according to claim 4, wherein said polyelectrolytes comprise nucleic acid, or nucleic acid strands having 5 kilo bases or more or 5 kilobase pairs or more, or 10 kilo bases or more or 10 kilobase pairs or more, and wherein said polyelectrolytes present in the liquid medium at step a) are obtained after or during a step of nucleic acid amplification, said amplification being a real-time quantitative amplification or comprising at least one of: a Reverse transcription, a Polymerase Chain Reaction amplification, an isothermal nucleic acid amplification, a rolling circle amplification, a branched rolling circle amplification, a circle to circle amplification, a LAMP NASBA TMA, SMART, HAD, RPA, CPA, SMART-AMP, RCA, HRCA, RAM, SDA, NEAR, NEMA, ICA, EXPAR, BAD AMP, or PG-RCA amplification, or nucleic acid amplification methods using Phi29 DNA polymerase.

7. A method according to claim 1, wherein the spatial and/or temporal fluctuations measured at step b) are those of an electrical variable,
   or
   the spatial and/or temporal fluctuations measured at step b) are those of an optical variable.

8. A method according to claim 1, wherein the stimulating electrical field applied at step a):

is a continuous or an alternating electrical field of frequency less than or equal to 1000 Hz, and/or
has an intensity greater than or equal to 50 V/cm, and/or
comprises a superposition of at least a first and a second electrical field components with different frequencies, the second electrical field component having an amplitude that is lower than the amplitude of the first electrical field component and the second electrical field component being either continuous or having a frequency that is lower than the frequency of the first electrical field component.

9. A method according to claim 1, the variable being electrical and the fluctuations of the electrical variable being measured at step b) by at least two electrodes (10) in direct electric contact with the liquid medium.

10. A method according to claim 1, the fluctuations of the electrical variable being measured at step b) by at least two electrodes facing each other, along an axis that is transverse to a direction of the stimulating electrical field.

11. A method according to claim 1, the variable being electrical and the fluctuations of the electrical variable being measured at step b) by at least two electrodes located at different positions along an axis parallel to a direction of the electrical field, the stimulating electrical field, applied at step a).

12. A method according to claim 1, wherein the stimulating electrical field, applied at step a), is applied by electrodes that are different from the electrodes that measure the fluctuations of the electrical variable at step b).

13. A method according to claim 1, the variable being electrical and the fluctuations of the electrical variable being measured at step b) by at least two electrodes polarized by an alternative polarization signal having a frequency that is different from a highest frequency component of the stimulating electrical field applied at step a).

14. A method according to claim 1, wherein the fluctuations of the variable are measured while the stimulating electrical field is applied, or the fluctuations of the variable are measured while the stimulating electrical field is not applied, the stimulating electrical field, not being applied during first periods, said first periods alternating with second periods during which the stimulating electrical field is applied.

15. A method according to claim 6, the nucleic acid being present in a medium comprising a buffer solution during the step of nucleic acid amplification, and the liquid medium used at step a) also comprising the same buffer solution.

16. A method according to claim 15, the buffer solution having a conductivity less than or equal to 1000 mS/m.

17. A method according to claim 15, the buffer solution comprising a polymerase active at a temperature of 37° C. or less.

18. A method according to claim 15, the buffer solution further comprising a ligase.

19. A method according to claim 17, the polymerase being a DNA polymerase.

20. A method according to claim 1, the space comprising a plurality of detection zones, each of the detection zones comprising a detector of at least one variable depending on the concentration of the macroions in the liquid medium.

21. A method according to claim 20, the liquid medium comprising different types of macroions to be detected, and compounds configured to interact with the macroions being present in each of the detection zones, the compounds present in one detection zone being different from the compounds present in another detection zone.

22. A method according to claim 21, the macroions to be detected being nucleic acids and the compounds being configured to interact with different nucleotide sequences of said nucleic acids.

23. A method according to claim 20, the space being elongated along a longitudinal axis and the detection zones succeeding each other along the longitudinal axis.

24. A method according to claim 20, the space comprising a plurality of sub-channels each comprising a detection zone.

25. A method according to claim 20, the spatial and/or temporal fluctuations within the liquid medium of at least one variable depending on the concentration of said macroions in the liquid medium being measured simultaneously among each of the detection zones.

26. A method according to claim 20, the spatial and/or temporal fluctuations within the liquid medium of at least one variable depending on the concentration of said macroions in the liquid medium being measured sequentially among each of the detection zones.

27. A method according to claim 20, the spatial and/or temporal fluctuations within the liquid medium of at least one variable depending on the concentration of said macroions in the liquid medium being measured among each of the detection zones and step c) comprising processing said spatial and/or temporal fluctuations measured from the plurality of detection zones.

28. A method according to claim 6, the nucleic acids to be aggregated and detected comprising an intercalating agent.

29. A method according to claim 9, the electrodes being coated with at least one layer comprising a surface-treating agent.

30. A method according to claim 29, the surface-treating agent being a hydrogel or a surfactant.

31. A method according to claim 1, the stimulating electrical field also inducing displacement of the macroion aggregates in the liquid medium.

32. A method according to claim 1, the spatial and/or temporal fluctuations measured at step b) being non-periodic.

33. A method according to claim 32, the spatial and/or temporal fluctuations measured at step b) being random.

34. A device for carrying out the method according to claim 1, comprising:
    a space to receive a liquid medium,
    at least two electrodes for generating a stimulating electrical field to induce formation of macroion aggregates from a macroion dispersion in the liquid medium, said pair of electrodes being connected to a first power supply,
    a detector of an electrical variable, comprising a plurality of electrodes to measure spatial and/or temporal fluctuations of the electrical variable induced by the presence of the macroion aggregates in the liquid medium, said plurality of electrodes being identical to or different from the electrodes for generating the stimulating electrical field, and
    a digital processor to perform a time-dependent or a space dependent analysis, or an autocorrelation on the variations of the electrical variable or on the image issued from an imaging detector, or on the output of an integrative optical detector.

35. A device for carrying out the method according to claim 1, comprising:
    a space to receive a liquid medium, the space comprising a liquid medium which contains a plurality of macroion,
    at least two electrodes for generating a stimulating electrical field to induce formation of macroion aggregates from a macroion dispersion in the liquid medium, said pair of electrodes being connected to a power supply,
    an optical detector, a camera, or an integrative optical detector, and
    a digital processor to perform a wavelet analysis, or an autocorrelation on the variations on an image issued from the optical detector, or on the output of the integrative optical detector.

36. A method of detecting macroions in a liquid medium contained in a space, said method comprising:
    a) submitting the liquid medium to a stimulating electrical field to induce formation of aggregates of macroions and displacement of said macroion aggregates in the liquid medium,
    b) measuring, in a detection zone of the space, spatial and/or temporal fluctuations within the liquid medium of at least one variable depending on the concentration of said macroions in the liquid medium, and
    c) determining, based on these fluctuations, the presence of the macroions.

* * * * *

SEQUENCE LISTING

<160> NUMBER OF SEQ ID NOS: 9

<210> SEQ ID NO 1
<211> LENGTH: 27
<212> TYPE: DNA
<213> ORGANISM: artificial sequence
<220> FEATURE:
<223> OTHER INFORMATION: primer

<400> SEQUENCE: 1
gaccatcggg gtaaaaccgt ctatgac                                    27

<210> SEQ ID NO 2
<211> LENGTH: 27
<212> TYPE: DNA
<213> ORGANISM: artificial sequence
<220> FEATURE:
<223> OTHER INFORMATION: Primer

<400> SEQUENCE: 2

```
atgacgactt attgccgctc tgttccc                                          27

<210> SEQ ID NO 3
<211> LENGTH: 90
<212> TYPE: DNA
<213> ORGANISM: Artificial sequence
<220> FEATURE:
<223> OTHER INFORMATION: Padlock probe

<400> SEQUENCE: 3
ctgccatctt aacaaaccct ttcctctatg attactgacc tacgacctca atgctgctgc      60
tgtactactc ttctatgcga ttaccgggct                                       90

<210> SEQ ID NO 4
<211> LENGTH: 17
<212> TYPE: DNA
<213> ORGANISM: artificial sequence
<220> FEATURE:
<223> OTHER INFORMATION: 5'-end of a ligation template

<400> SEQUENCE: 4
gtttgttaag atggcag                                                     17

<210> SEQ ID NO 5
<211> LENGTH: 13
<212> TYPE: DNA
<213> ORGANISM: artificial sequence
<220> FEATURE:
<223> OTHER INFORMATION: 3'-end of a ligation template

<400> SEQUENCE: 5
agcccggtaa tcg                                                         13

<210> SEQ ID NO 6
<211> LENGTH: 17
<212> TYPE: DNA
<213> ORGANISM: artificial sequence
<220> FEATURE:
<223> OTHER INFORMATION: Portion of a padlock probe

<400> SEQUENCE: 6
caaacaattc taccgtc                                                     17

<210> SEQ ID NO 7
<211> LENGTH: 13
<212> TYPE: DNA
<213> ORGANISM: artificial sequence
<220> FEATURE:
<223> OTHER INFORMATION: Portion of a Padlock probe

<400> SEQUENCE: 7
tcgggccatt agc                                                         13

<210> SEQ ID NO 8
<211> LENGTH: 90
<212> TYPE: DNA
<213> ORGANISM: artificial sequence
<220> FEATURE:
<223> OTHER INFORMATION: Probe

<400> SEQUENCE: 8
ctgccatctt aacaaaccct ttcctctatg attactgacc tacgacctca atgctgctgc      60
tgtactactc ttctatgcga ttaccgggct                                       90
```

```
<210> SEQ ID NO 9
<211> LENGTH: 30
<212> TYPE: DNA
<213> ORGANISM: artificial sequence
<220> FEATURE:
<223> OTHER INFORMATION: Target

<400> SEQUENCE: 9
gtttgttaag atggcagagc ccggtaatcg                              30
```